United States Patent
Hakoshima et al.

(10) Patent No.: US 10,123,695 B2
(45) Date of Patent: Nov. 13, 2018

(54) DIAGNOSIS SUPPORTING DEVICE AND METHOD OF SUPPORTING DIAGNOSIS

(71) Applicant: JVC KENWOOD Corporation, Yokohama-shi, Kanagawa (JP)

(72) Inventors: Shuji Hakoshima, Yokohama (JP); Katsuyuki Shudo, Yokohama (JP); Masaru Ninomiya, Yokohama (JP)

(73) Assignee: JVC KENWOOD Corporation, Yokohama-shi (JP)

( * ) Notice: Subject to any disclaimer, the term of this patent is extended or adjusted under 35 U.S.C. 154(b) by 187 days.

(21) Appl. No.: 15/006,333

(22) Filed: Jan. 26, 2016

(65) Prior Publication Data

US 2016/0150956 A1 Jun. 2, 2016

Related U.S. Application Data

(63) Continuation of application No. PCT/JP2014/069978, filed on Jul. 29, 2014.

(30) Foreign Application Priority Data

Jul. 31, 2013 (JP) .................................. 2013-159941
Feb. 27, 2014 (JP) .................................. 2014-036635

(51) Int. Cl.
*A61B 3/113* (2006.01)
*A61B 3/14* (2006.01)
(Continued)

(52) U.S. Cl.
CPC ............ *A61B 3/113* (2013.01); *A61B 3/0025* (2013.01); *A61B 3/0058* (2013.01); *A61B 3/14* (2013.01);
(Continued)

(58) Field of Classification Search
CPC ....................................................... A61B 3/113
(Continued)

(56) References Cited

U.S. PATENT DOCUMENTS 4,836,670 A * 6/1989 Hutchinson ............ A61B 3/113
351/210
5,898,423 A * 4/1999 Tognazzini ............. G06F 3/013
345/158

(Continued)

FOREIGN PATENT DOCUMENTS

JP 2005-185431 7/2005
JP 2005-198743 7/2005

(Continued)

OTHER PUBLICATIONS

Extended European Search Report for European Patent Application No. 14831584.9 dated Feb. 1, 2017.

(Continued)

*Primary Examiner* — Zachary Wilkes
(74) *Attorney, Agent, or Firm* — Amin, Turocy & Watson LLP

(57) ABSTRACT

A display, imaging units that capture a subject, an eye gaze detector that detects an eye gaze direction of the subject, from the captured image captured by the imaging units, a gaze point detector that detects a gaze point of the subject in a display region of the display, based on the eye gaze direction, an output controller that displays any of a plurality of diagnosis images on the display, selects the diagnosis image to be displayed next according to a position of the gaze point detected when the diagnosis image is displayed, from the plurality of diagnosis images, and further displays the selected diagnosis image on the display, and an evaluator (Continued)

that calculates an evaluation value of the subject, based on the gaze point detected by the gaze point detector when the diagnosis image is displayed.

6 Claims, 20 Drawing Sheets

(51) Int. Cl.
*A61B 3/00* (2006.01)
*G06K 9/00* (2006.01)

(52) U.S. Cl.
CPC ....... *G06K 9/0061* (2013.01); *G06K 9/00604* (2013.01)

(58) Field of Classification Search
USPC .................................................. 351/209, 246
See application file for complete search history.

(56) References Cited

U.S. PATENT DOCUMENTS

| 9,538,947 B2* | 1/2017 | Mori ........................ A61B 5/16 |
| 2011/0242486 A1 | 10/2011 | Ebisawa |
| 2014/0213930 A1 | 7/2014 | Mori et al. |

FOREIGN PATENT DOCUMENTS

| JP | 2008-125619 | 6/2008 |
| JP | 2011-206542 | 10/2011 |
| JP | 2013-052116 | 3/2013 |

OTHER PUBLICATIONS

International Search Report for International Patent Application No. PCT/JP2014/069978 dated Nov. 11, 2014, 5 pages.
Written Opinion for International Patent Application No. PCT/JP2014/069978 dated Nov. 11, 2014, 3 pages.

\* cited by examiner

DIAGNOSIS SUPPORTING DEVICE AND METHOD OF SUPPORTING DIAGNOSIS

CROSS-REFERENCE TO RELATED APPLICATION(S)

This application is a continuation of PCT international application Ser. No. PCT/JP2014/069978 filed on Jul. 29, 2014 which designates the United States, incorporated herein, by reference, and which claims the benefit of priority from Japanese Patent Application No. 2013-159941, filed on Jul. 31, 2013 and Japanese Patent Application No. 2014-036635, filed on Feb. 27, 2014, incorporated herein by reference.

BACKGROUND OF THE INVENTION

1. Field of the Invention

The present invention relates to a diagnosis supporting device and a method of supporting diagnosis.

2. Description of the Related Art

In recent years, it is said that the number of developmentally disabled persons is increasing. The developmental disorder is known that symptoms can be relieved by early discovery and start of rehabilitation, and an effect to adapt to society can become high. Our country has been striving to early discovery by a medical interview at the time of medical examination of 1 and a half years old, and the like. However, there are problems such as psychiatrist shortage and taking time for the medical interview, and an effect thereof cannot be said to be sufficient. Therefore, an objective and efficient diagnosis supporting device of the developmental disorder has been sought.

For the early discovery of the developmental disorder, it is ideal to have diagnosis at the time of the medical examination of 1 and a half years old, for example. An example of a characteristic of a developmentally disabled child includes not making eye contact with a facing person (looking away of eye gaze). Further, the developmentally disabled child is known to have a preference for geometrical pattern pictures to person pictures.

Further, methods of supporting diagnosis of developmental disorder by application of methods of capturing a face of a human with a camera and detecting a gaze point by calculation of positions of a corneal reflection and a pupil have been proposed.

However, a subject of about 1 and a half years old has limited power of concentration. Therefore, it is necessary to perform diagnosis as briefly as possible. However, the conventional methods of detecting a gaze point may not be able to support the diagnosis in a short time, and methods of supporting diagnosis in a shorter time have been sought.

Therefore, there is a need for a diagnosis supporting device and a method of supporting diagnosis that enable diagnosis in a short time.

SUMMARY OF THE INVENTION

It is an object of the present invention to at least partially solve the problems in the conventional technology.

A diagnosis supporting device includes a display, an imaging unit configured to capture a subject, an eye gaze detector configured to detect an eye gaze direction of the subject, from a captured image captured by the imaging unit, a gaze point detector configured to detect a gaze point of the subject in a display region of the display, based on the eye gaze direction, an output controller configured to display any of a plurality of diagnosis images on the display, select the diagnosis image to be displayed next according to a position of the gaze point detected when the diagnosis image is displayed, from the plurality of diagnosis images, and display the selected diagnosis image on the display, and an evaluator configured to calculate an evaluation value of the subject, based on the gaze point detected by the gaze point detector of when the diagnosis image is displayed.

The diagnosis supporting device and the method of supporting diagnosis according to the present invention exert an effect to perform diagnosis in a short time.

The above and other objects, features, advantages and technical and industrial significance of this invention will be better understood by reading the following detailed description of presently preferred embodiments of the invention, when considered in connection with the accompanying drawings.

DETAILED DESCRIPTION OF THE PREFERRED EMBODIMENTS

Hereinafter, embodiments of a diagnosis supporting device and a method of supporting diagnosis according to the present invention will be described in detail based on the drawings. Note that the present invention is not limited by these embodiments.

First Embodiment

Conventionally, an eye gaze of a subject to single content displayed on a monitor is detected, and developmental disorder is determined according to coordinates that the subject has gazed at. However, in a case of a subject at an early age, there is a problem that it is difficult to cause the subject to gaze at the monitor for a long time during diagnosis.

Therefore, a diagnosis supporting device of a first embodiment selects a diagnosis image (content) to be displayed next according to the position of the detected gaze point, from a plurality of diagnosis images. For example, a plurality of indexes is provided to content (a moving image or the like) to be viewed by the subject, and the content is virtually divided into a plurality of diagnosis images. Then, an unnecessary diagnosis image is skipped, according to movement of the eye gaze of the subject detected when a certain diagnosis image is being displayed, and a diagnosis image corresponding to the next index is displayed. In this way, by selectively presenting a portion more suitable for diagnosis support, diagnosis time can be reduced. As a result, a decrease in the power of concentration can be prevented, and accuracy of the diagnosis can be improved.

Figure 1:
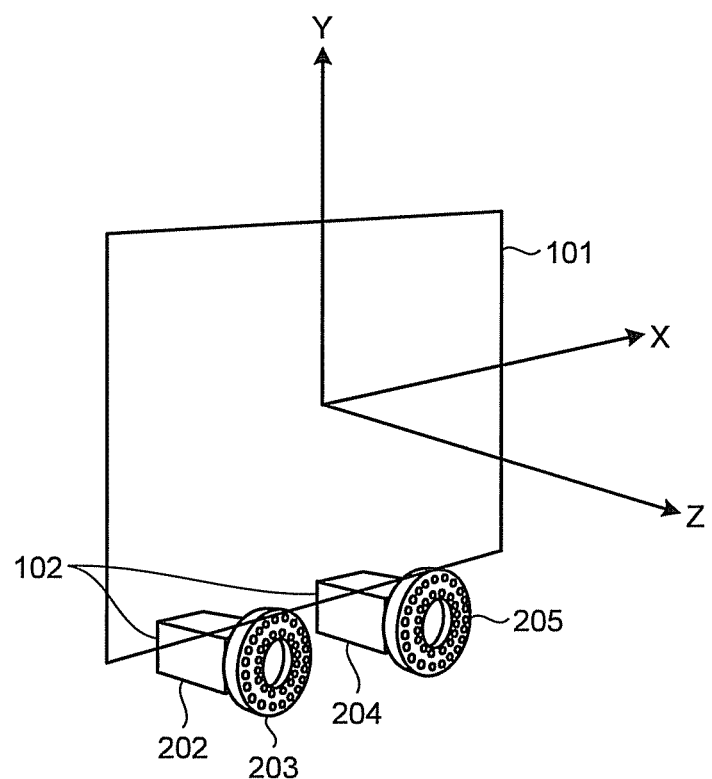
FIG. 1 is a diagram illustrating an example of an arrangement of a display, stereo cameras, and a light source used in a first embodiment.

FIG. 1 is a diagram illustrating an example of an arrangement of a display, stereo cameras, and a light source used in the first embodiment. As illustrated in FIG. 1, in the present embodiment, a pair of stereo cameras 102 is arranged at a lower side of a display screen 101. The stereo cameras 102 are imaging units that can perform stereo capturing with infrared rays, and includes a right camera 202 and a left camera 204.

Infrared light emitting diode (LED) light sources 203 and 205 are respectively arranged immediately before respective lenses of the right camera 202 and the left camera 204 in a circumferential direction. The infrared LED light sources 203 and 205 include an inner circumferential LED and an outer circumferential LED having mutually different wavelengths to be emitted. A pupil of a subject is detected with the infrared LED light sources 203 and 205. As a method of detecting a pupil, a method described in Japanese Laid-open Patent Publication No. 2008-125619 or the like can be applied.

In detecting an eye gaze, a space is expressed in coordinates, and a position is identified. In the present embodiment, a coordinate in an up and down direction is a Y coordinate (the up direction is +), a coordinate in a transverse direction is an X coordinate (the right direction is +), and a coordinate in a depth direction is a Z coordinate (the front side is +), where a middle position on the display screen 101 is the origin.

Figure 2:
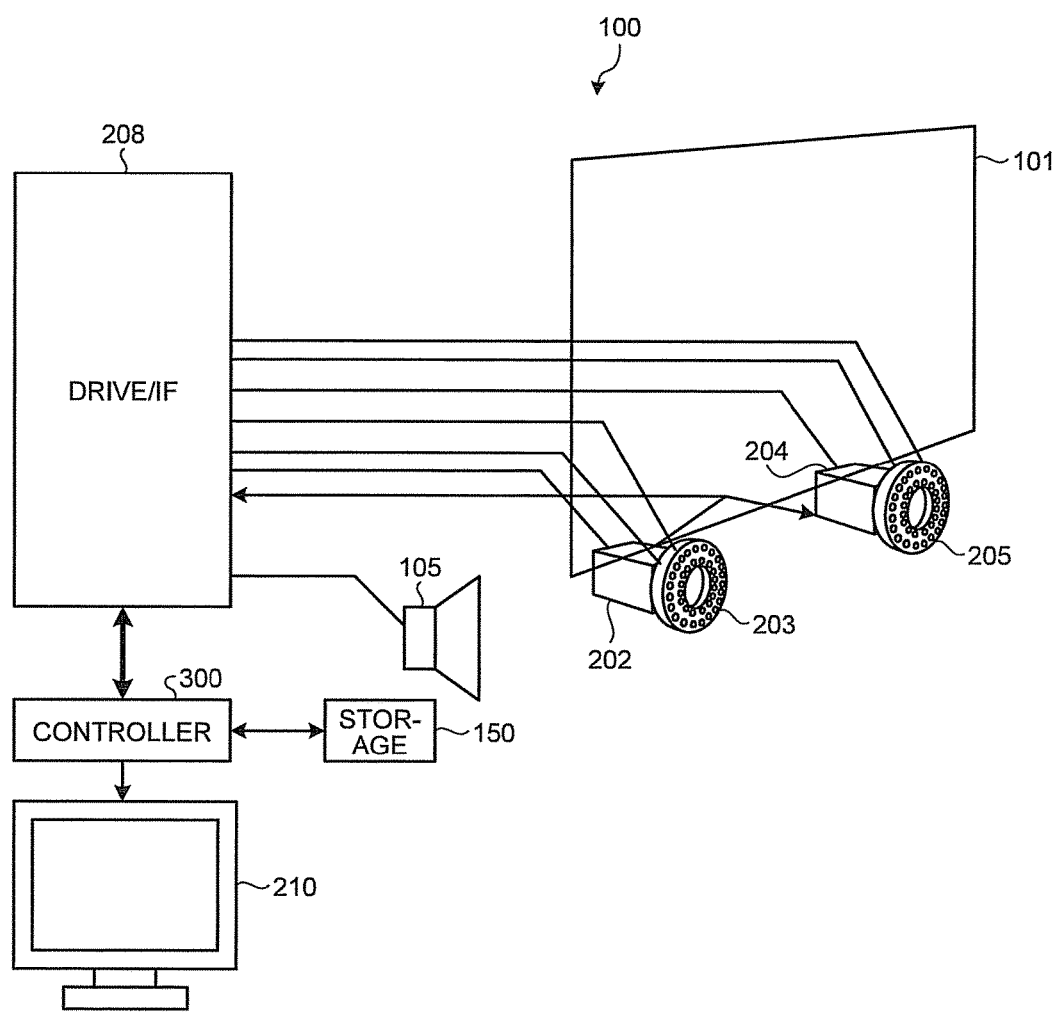
FIG. 2 is a diagram illustrating an outline of functions of a diagnosis supporting device of the first embodiment.

FIG. 2 is a diagram illustrating an outline of functions of a diagnosis supporting device 100. FIG. 2 illustrates a part of the configuration illustrated in FIG. 1, and a configuration used for driving of the aforementioned configuration. As illustrated in FIG. 2, the diagnosis supporting device 100 includes the right camera 202, the left camera 204, the infrared LED light sources 203 and 205, a speaker 105, a drive/interface (IF) 208, a controller 300, a storage 150, a display 210. In FIG. 2, a positional relationship of the display screen 101 with the right camera 202 and the left camera 204 is illustrated in an easy-to-understand manner. However, the display screen 101 is a screen displayed on the display 210. Note that the driver and the IF may be an integrated body or separate bodies.

The speaker 105 functions as an audio output unit that outputs an audio and the like for prompting the subject to pay attention, at the time of calibration and the like.

The drive/IF 208 drives units included in the stereo cameras 102. Further, the drive/IF 208 serves as an interface between the units included in the stereo cameras 102, and the controller 300.

The storage 150 stores various types of information such as a control program, a measurement result, and a diagnosis support result. The storage 150 stores an image to be displayed on the display 210, and the like. The display 210 displays various types of information such as an object image for diagnosis, and the like.

Figure 3:
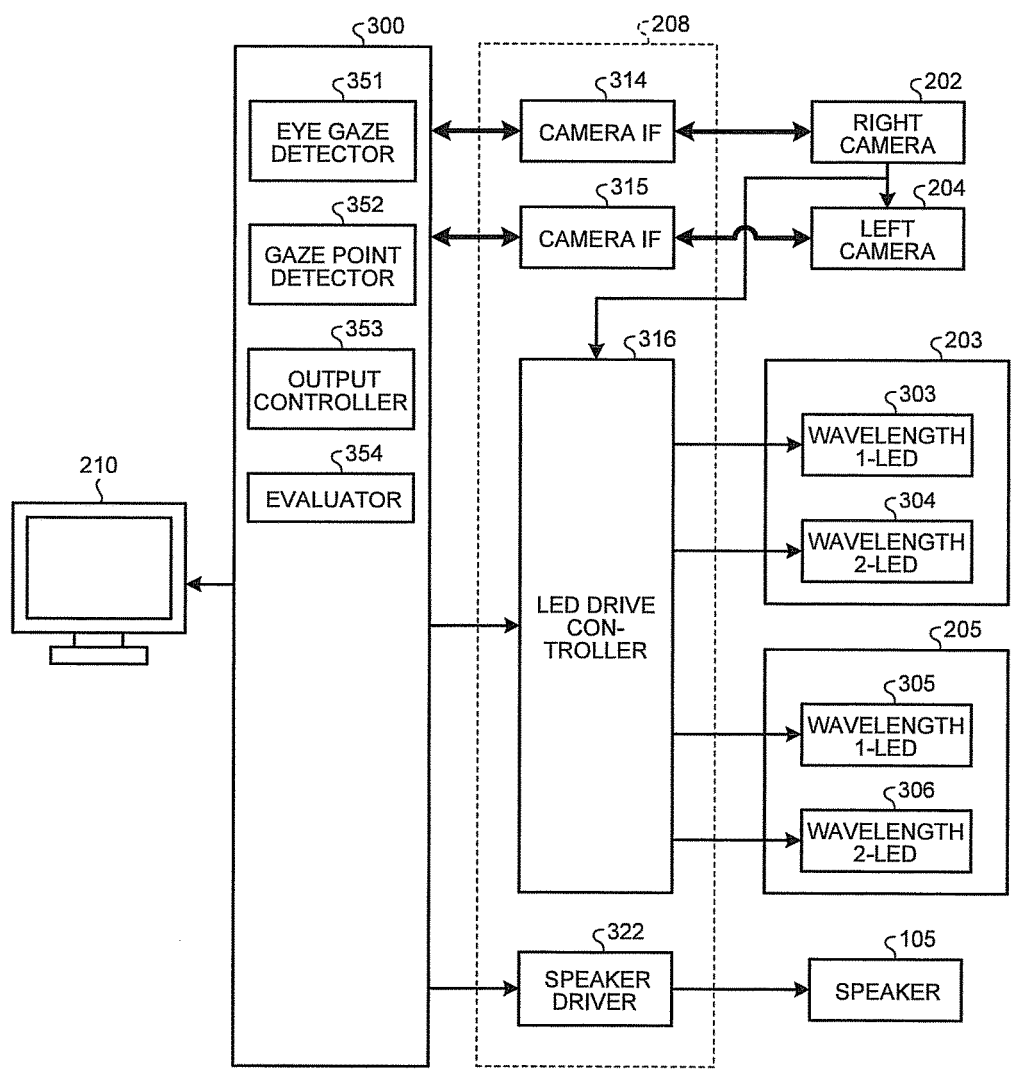
FIG. 3 is a block diagram illustrating an example of detailed functions of respective units illustrated in FIG. 2.

FIG. 3 is a block diagram illustrating an example of detailed functions of the respective units illustrated in FIG. 2. As illustrated in FIG. 3, the display 210 and the drive/IF 208 are connected to the controller 300. The drive/IF 208 includes camera IFs 314 and 315, an LED drive controller 316, and a speaker driver 322.

The right camera 202 and the left camera 204 are connected to the drive/IF 208 respectively through the camera IFs 314 and 315. The drive/IF 208 drives these cameras to capture the subject.

The infrared LED light source 203 includes a wavelength 1-LED 303 and a wavelength 2-LED 304. The infrared LED light source 205 includes a wavelength 1-LED 305 and a wavelength 2-LED 306.

The wavelength 1-LEDs 303 and 305 perform irradiation with infrared rays of a wavelength 1. The wavelength 2-LEDs 304 and 306 perform irradiation with infrared rays of a wavelength 2.

The wavelength 1 and the wavelength 2 are a wavelength of less than 900 nm and a wavelength of 900 nm or more, respectively. When the pupil is irradiated with the infrared rays of the wavelength of less than 900 nm, and reflection light reflected at the pupil is captured, a brighter pupil image can be obtained, compared with a case where the pupil is irradiated with the infrared rays of the wavelength of 900 nm or more, and reflection light reflected at the pupil is captured. Note that wavelengths of the infrared rays to be irradiated are not limited to the above wavelengths, and any wavelengths may be used as long as a difference can be obtained between a result of a case where the pupil is irradiated with the infrared rays of the wavelength 1 and the reflection light reflected at the pupil is captured, and a result of a case where the pupil is irradiated with the infrared rays of the wavelength 2 and the reflection light reflected at the pupil is captured.

The speaker driver 322 drives the speaker 105. Note that the diagnosis supporting device 100 may include an interface (printer IF) for being connected with a printer as a print unit. Further, the printer may be included inside the diagnosis supporting device 100.

The controller 300 controls the entire diagnosis supporting device 100. The controller 300 includes an eye gaze detector 351, a gaze point detector 352, an output controller 353, and an evaluator 354.

The eye gaze detector 351 detects an eye gaze (eye gaze direction) of the subject, from the captured images captured by the imaging units (stereo cameras 102). Processing of detecting an eye gaze includes processing of detecting a position of an eye of the subject. The gaze point detector 352 detects a gaze point of the subject, using the detected eye gaze direction. The gaze point detector 352 detects a gaze point that is a point that the subject gazes at, of an object image displayed on the display screen 101. As an eye gaze detection method by the eye gaze detector 351, and a gaze point detection method by the gaze point detector 352, any conventionally used methods can be applied. Hereinafter, a case of detecting the eye gaze direction and the gaze point of the subject, using the stereo cameras, similarly to Japanese Laid-open Patent Publication No. 2005-198743, will be exemplarily described.

In this case, first, the eye gaze detector 351 detects the eye gaze direction of the subject, from the images captured by the stereo cameras 102. The eye gaze detector 351 detects the eye gaze direction of the subject, using the methods described in Japanese Laid-open Patent Publication No. 2005-185431 and Japanese Laid-open Patent Publication No. 2008-125619, and the like, for example. To be specific, the eye gaze detector 351 obtains a difference between an image obtained such that the pupil is irradiated with the infrared rays of the wavelength 1 and captured, and an image obtained such that the pupil is irradiated with the infrared rays of the wavelength 2 and captured, and generates an image with a clarified pupil image. The eye gaze detector 351 calculates a position of the pupil of the subject (a position of the eye) by a stereoscopic technique, using two images generated as described above from the images captured by the right and left cameras (the right camera 202 and the left camera 204), respectively. Further, the eye gaze detector 351 calculates a position of a corneal reflection of the subject, using the images captured by the right and left cameras. The eye gaze detector 351 then calculates an eye gaze vector that indicates the eye gaze direction of the subject, from the position of the pupil of the subject and a corneal reflection position.

Note that a method of detecting the position of the eye and the eye gaze of the subject is not limited to the above method. For example, the position of the eye of the subject and the eye gaze may be detected, by an analysis of an image captured using visible light, instead of the infrared rays.

The gaze point detector 352 detects an intersection point of the eye gaze vector expressed in a coordinate system like FIG. 1, and an XY plane, as the gaze point of the subject, for example. When the gaze point detector 352 can obtain eye gaze directions of both eyes, the gaze point detector 352 may measure the gaze point by obtaining an intersection point of right and left eye gazes of the subject.

Figure 4:
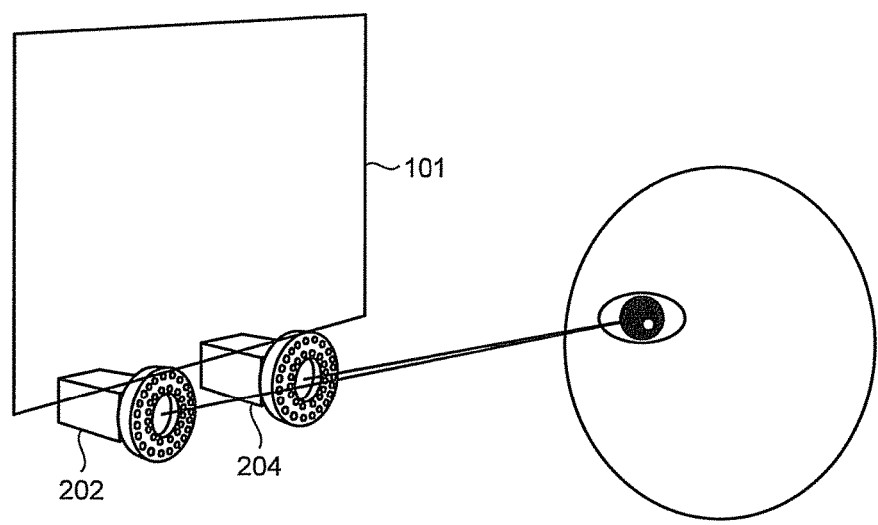
FIG. 4 is a diagram illustrating an example of detection of an eye and a distance of when two cameras are used.

FIG. 4 is a diagram illustrating an example of detection of an eye and a distance of when using the two cameras (the right camera 202 and the left camera 204). A camera calibration theory by a stereo calibration method is applied to the two cameras, and a camera parameter is obtained in advance. As the stereo calibration method, any conventionally used method such as a method using a camera calibration theory of Tsai can be applied. Three-dimensional coordinates of the eye in a world coordinate system can be obtained using the position of the eye detected from the image captured by the right camera 202, the position of the eye detected from the image captured by the left camera 204, and the camera parameter. Accordingly, the distance between the eye and the stereo cameras 102, and pupil coordinates can be estimated. The pupil coordinates are coordinate values that indicate the position of the eye (pupil) of the subject on the XY plane. The pupil coordinates can be coordinate values of the position of the eye expressed in the world coordinate system being projected onto the XY plane, for example. Usually, the pupil coordinates of the right and left both eyes are obtained. A diagnosis image is displayed on the display screen 101.

Note that the diagnosis image may be either a still image or a moving image (picture). However, the moving image is desirable because a subject can easily gaze at the moving image. The diagnosis image may include a plurality of diagnosis images that is temporally and continuously displayed, for example. As described above, one picture (a moving image or the like) may be divided and used as the plurality of diagnosis images. Each of the plurality of diagnosis images is an image with which whether the subject has the developmental disorder can be diagnosed. For example, at least a part of the plurality of diagnosis images may include an image of a person (person picture) and an image of a geometrical pattern (geometrical pattern picture). A natural image may be used as an image other than the geometrical pattern that the subject with the developmental disorder has a preference. The natural image may just be an image of a natural object or an image that is associated with a natural object, other than the geometrical image. For example, an image (a still image or a moving image) obtained by capturing of a person, an animal, a plant, a landscape of nature, or the like, with a camera, may be used as the natural image. Further, an image (a still image or a moving image) of a character that mimics a person or an animal may be used as the natural image.

Referring back to FIG. 3, the output controller 353 controls outputs of various types of information for the display 210, the speaker 105, and the like. For example, the output controller 353 controls outputs to the display 210, such as the diagnosis image and an evaluation result by the evaluator 354. The output controller 353 displays any of the plurality of diagnosis images on the display, and selects a diagnosis image to be displayed next, according to positions of a gaze point detected when the diagnosis image is being displayed, from a plurality of diagnosis images. The output controller 353 then displays the selected diagnosis image on the display, and repeats similar processing.

As a method of selecting the diagnosis image to be displayed next, a following method can be applied, for example. First, the output controller 353 classifies the plurality of diagnosis images into any of a plurality of groups. For example, the output controller 353 may perform classification such that similar diagnosis images belong to the same group. Further, the output controller 353 may perform classification such that a plurality of diagnosis images (a first diagnosis image and a second diagnosis image) in which two images (for example, a person picture and a geometrical pattern picture) are arranged to be symmetrical to a predetermined point or line belongs to the same group.

The output controller 353 then switches, according to the positions of the gaze point detected when the diagnosis image classified in a certain group (predetermined group) is being displayed, whether selecting another diagnosis image classified in the same group (predetermined group), or selecting a diagnosis image classified in another group (another group different form the predetermined group, of the plurality of groups), as the diagnosis image to be displayed next. Accordingly, when it is determined that the subject has no tendency of the developmental disorder for the diagnosis image belonging to the certain group, or the diagnosis with the diagnosis image is difficult, display of the remaining diagnosis image of the group can be skipped.

Various conditions can be applied as a condition to perform switching. For example, a condition that another diagnosis image in the same group is selected when the positions of the detected gaze point are matched with a pattern of positions of a gaze point of a subject with the developmental disorder, and diagnosis image of the next group is selected in other cases may be applied.

As the pattern of positions of a gaze point of a subject with the developmental disorder, a pattern of a ratio of the gaze points included in a region of an eye included in a person picture being less than a predetermined threshold (for example, 80%) can be applied, for example. An applicable pattern is not limited to the above example, and any pattern is applicable as long as tendency of the developmental disorder can be determined from the ratio of the gaze point included in a specific region in a predetermined period. For example, in a case of a diagnosis image that includes a person picture and a geometrical pattern picture, a pattern of a ratio of the gaze point included in the person picture being a predetermined threshold or less may be used. The ratio of the gaze point included in a certain region (image) is obtained by, for example, the number of gaze points detected in the region (or a total time in which the gaze point is detected within the region), to the total number of the detected gaze points (or a total time in which the gaze point is detected).

The evaluator 354 calculates an evaluation value as an index related to the degree of the developmental disorder, based on the diagnosis image and the gaze point detected by the gaze point detector 352. The evaluator 354 calculates the evaluation value, based on positions of the gaze point of the subject of when the diagnosis image like FIG. 5 described below is displayed. For example, the evaluator 354 calculates a ratio of looking at a predetermined region (a region of an eye, for example) within the diagnosis image, as the evaluation value. The evaluator 354 calculates the evaluation value that indicates the possibility of the developmental disorder is higher as the evaluation value is lower. The evaluator 354 may employ an average value or a total value of values calculated for a plurality of respective diagnosis images, as a final evaluation value. The evaluator 354 may just calculate the evaluation value, based on the diagnosis image and the gaze point, and a calculation method thereof is not limited to the embodiment.

Figure 5:
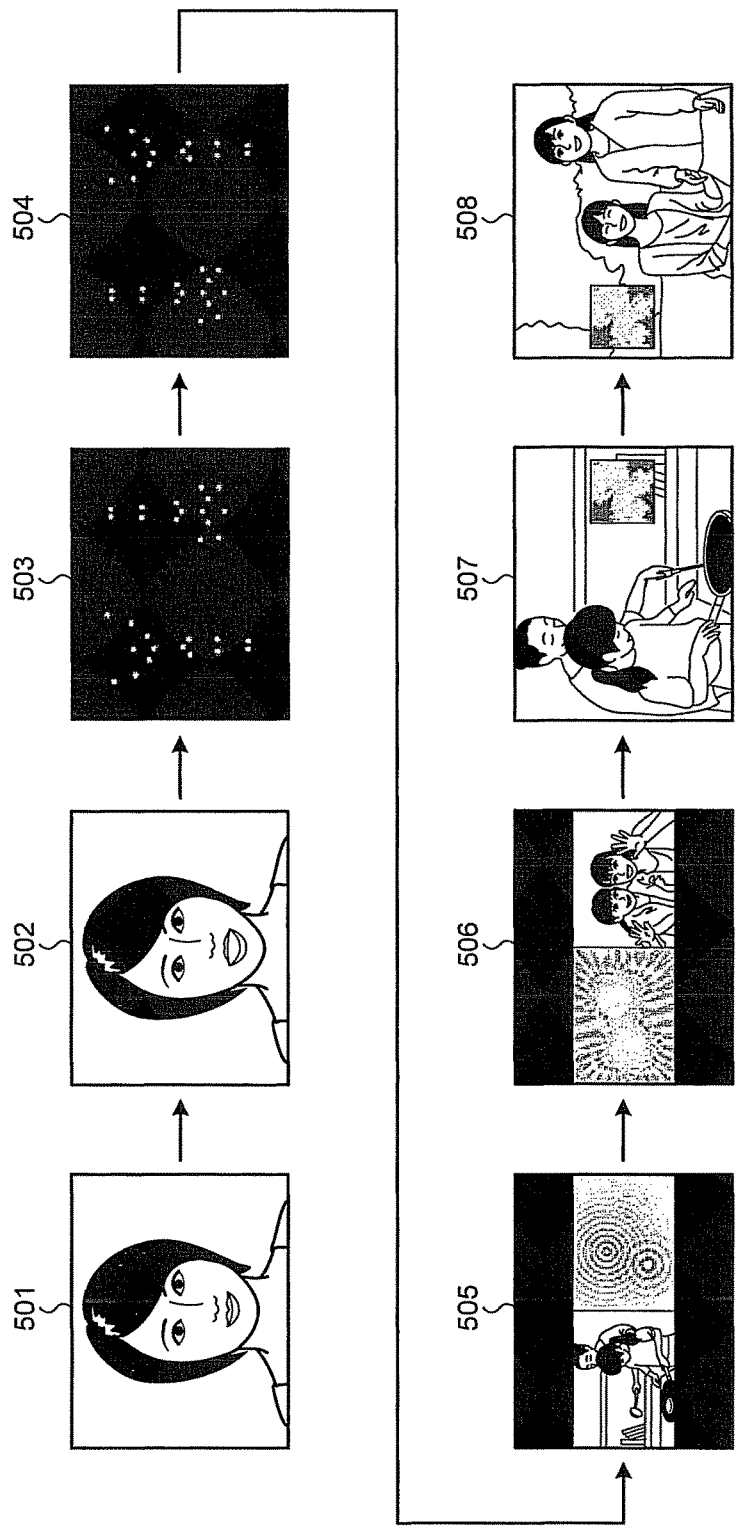
FIG. 5 is a diagram illustrating examples of diagnosis images.

FIG. 5 is a diagram illustrating examples of the diagnosis images. FIG. 5 illustrates an example of virtually dividing one continuous moving image into eight moving images (diagnosis images) by marking switching points of the diagnosis images with marks (indexes).

A diagnosis image 501 is a still image picture of a person. Which region of a region of an eye, a region of a mouse and the like included in the diagnosis image 501 the subject gazes at becomes an index of diagnosis (evaluation value). Typically, when the developmental disorder is suspected, the subject tends to gaze at a region other than the eye.

A diagnosis image 502 is a picture of a person talking to the subject. Similarly to the diagnosis image 501, which region of the region of an eye, the region of a mouse and the like included in the diagnosis image 502 the subject gazes at becomes an index of diagnosis. Typically, when the developmental disorder is suspected, the subject tends to gaze at a region other than the eye.

The left half of a diagnosis image 503 is a picture expressing a state where a person moves to music, using a plurality of points. The right half of the diagnosis image 503 is a picture upside down expressing a state where a person moves without harmonizing with music, using a plurality of points. The left-side picture is more likely to become a gazing object because the movement overlaps with movement of a normal full-length figure of a human. Therefore, frequencies of an eye gaze to the right and left pictures become an index. Meanwhile, when the developmental disorder is suspected, it is typically difficult for the subject to recognize the group of points as movement of a person, and there is less deviation of the gaze point.

A diagnosis image 504 is a picture in which the right and left images included in the diagnosis image 503 is interchanged. That is, the diagnosis image 503 and the diagnosis image 504 correspond to a plurality of diagnosis images arranged symmetrical to a line set in advance (a line in the up and down direction, which passes through a vicinity of the center of the diagnosis image). By use of such two diagnosis images, whether the eye gaze of the subject depends on a right and left positional relationship can be confirmed, and more accurate diagnosis can be performed.

A diagnosis image 505 is an diagnosis image in which a picture of persons is arranged on the left half, and a picture of a geometrical pattern is arranged on the right half. Frequencies of the eye gaze to the right and left pictures become an index of diagnosis. When the developmental disorder is suspected, it is typically considered that the subject has a preference for the picture of a geometrical pattern to the picture of persons.

A diagnosis image 506 is a diagnosis image in which a picture of a geometrical pattern is arranged on the left half, and a picture of persons is arranged on the right half, in an opposite manner to the diagnosis image 505. The pictures are slightly different from those of the diagnosis image 505. Similarly to the diagnosis image 504, the diagnosis image 506 is used to confirm whether the eye gaze position of the subject depends on the right and left positional relationship.

A diagnosis image 507 is a diagnosis image in which a picture of persons is arranged in the entire screen, and a picture of a geometrical pattern is arranged in a partial region. Frequencies of the eye gaze to the geometrical pattern picture and to a region other than the geometrical pattern picture become an index of diagnosis.

A diagnosis image 508 is a diagnosis image that displays a picture of a geometrical pattern in a position different from the diagnosis image 507. Similarly to the diagnosis image 504, the diagnosis image 508 is used to confirm whether the eye gaze position of the subject depends on the right and left positional relationship.

In the example of FIG. 5, the eight diagnosis images can be classified into the four groups below:

Group A: the diagnosis image 501 and the diagnosis image 502

Group B: the diagnosis image 503 and the diagnosis image 504

Group C: the diagnosis image 505 and the diagnosis image 506

Group D: the diagnosis image 507 and the diagnosis image 508

Each of the groups includes similar diagnosis images used to calculate a similar index (evaluation value). Note that the number of diagnosis images included in each of the groups is not limited to two, and three or more diagnosis images may be included.

For example, one of the diagnosis image 502 belonging to the same group, and the diagnosis image 503 of the next group B is selected as a diagnosis image to be displayed next, according to the position of the gaze point detected when the diagnosis image 501 of the group A is being displayed. In this case, the group A is a predetermined group, and the group B is another group different from the predetermined group, of the plurality of groups. Similarly, one of the diagnosis image 504 belonging to the same group, and the diagnosis image 505 of the next group C is selected as a diagnosis image to be displayed next according to the position of the gaze point detected when the diagnosis image 503 of the group B is being displayed. In this case, the group B is the predetermined group, and the group C is the another group different from the predetermined group, of the plurality of groups. Similar processing is applied to the groups C and D.

Figure 6:
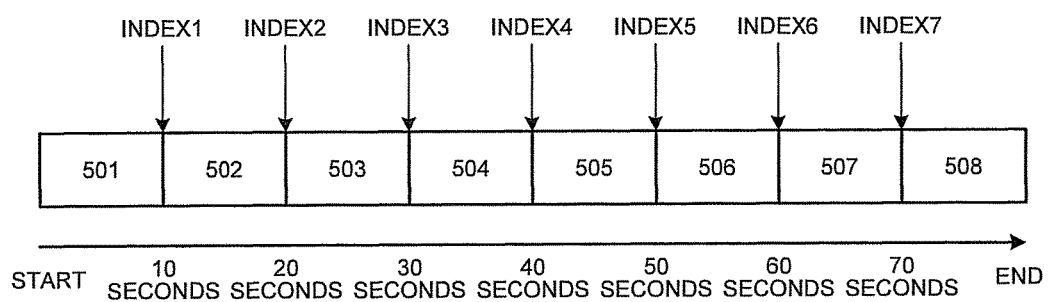
FIG. 6 is a diagram illustrating an example of a time chart of diagnosis images.

FIG. 6 is a diagram illustrating an example of a time chart of diagnosis images to be displayed. FIG. 6 is an example of a case where the diagnosis images 501 to 508 of FIG. 5 are displayed in order. A display time of each diagnosis image is 10 seconds, and the display is terminated in 80 seconds in total. To perform processing of reduction of time, indexes (INDEXES 1 to 7) are provided at the switching points of the diagnosis images. During display of each diagnosis image on the display 210, detection and diagnosis of the eye gaze of the subject are performed. Therefore, normally, it is necessary to cause the subject to gaze at the display 210 for 80 seconds at least. The present embodiment reduces this time by a method like below.

Figure 7:
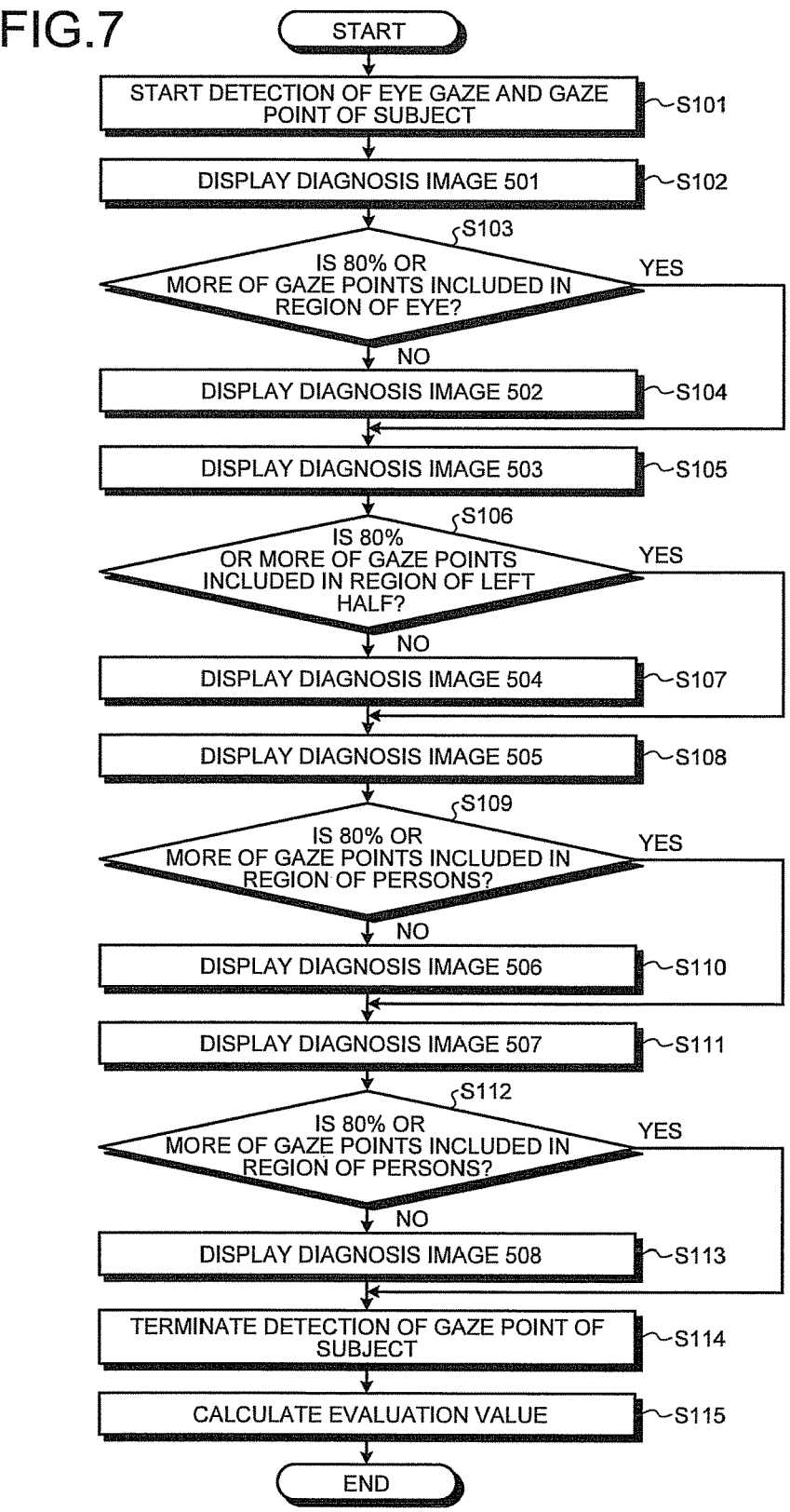
FIG. 7 is a flowchart illustrating an example of diagnosis supporting processing of the first embodiment.
Figure 8:
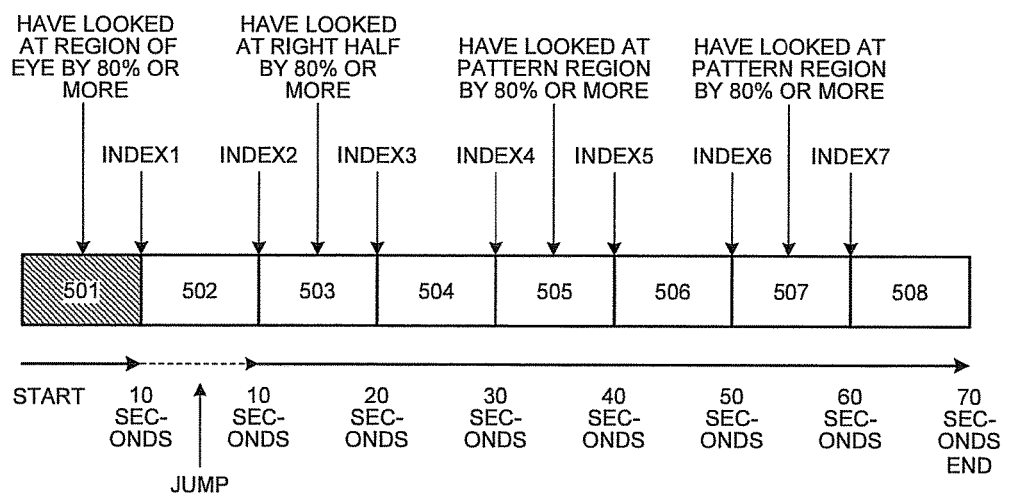
FIG. 8 is a diagram illustrating an example of a time chart of diagnosis images.

First, an example of reduction of diagnosis time, using a flowchart of FIG. 7 and a time chart of FIG. 8, will be described. FIG. 7 is a flowchart illustrating an example of diagnosis supporting processing of the first embodiment. FIG. 8 is a diagram illustrating an example of a time chart of a diagnosis image to be displayed.

First, the output controller 353 starts reproduction of a diagnosis image as illustrated in FIG. 5. Further, the eye gaze detector 351 and the gaze point detector 352 starts an operation to detect the eye gaze and the gaze point (step S101). The output controller 353 displays the diagnosis image 501 of FIG. 5, first (step S102).

The output controller 353 determines whether 80% or more of gaze point positions of the subject detected when the diagnosis image 501 is being displayed is included in the region of the eye of the person picture (step S103). Note that the threshold (80%) used for determination is an example and is not limited to the example. Further, when the diagnosis image is being displayed may be a part of the period in which the diagnosis image is being displayed. The same applies to the description below.

When 80% or more of the gaze point positions is not included in the region of the eye (No at step S103), the output controller 353 selects the diagnosis image 502, as the image to be displayed next, and displays the diagnosis image 502 (step S104). That is, when 80% or more of the gaze point positions is not included in the region of the eye, there is a possibility of the developmental disorder, and thus the output controller 353 displays the similar diagnosis image 502 again. Accordingly, more accurate diagnosis can be performed. After displaying the diagnosis image 502, the output controller 353 displays the diagnosis image 503 that is the image of the next group (step S105).

When 80% or more of the gaze point positions of the subject detected when the diagnosis image 501 is being displayed is included in the region of the eye (Yes at step S103), the output controller 353 skips the diagnosis image 502, selects the diagnosis image 503, as the image to be displayed next, and displays the diagnosis image 503 (step S105).

In the example of FIG. 8, the subject has looked at the region of the eye at a rate of 80% or more. Therefore, it is determined that there is no tendency of the developmental disorder for the diagnosis image 501, or the diagnosis with the diagnosis image 501 is difficult. Therefore, it is not effective to further display the diagnosis image 502 similar to the diagnosis image 501 to diagnose the developmental disorder. Therefore, the output controller 353 skips display of the diagnosis image 502, and jumps to a next picture position (INDEX 2). In the example of FIG. 8, the output controller 353 jumps from the INDEX 1 to the INDEX 2.

Next, the output controller 353 determines whether 80% or more of the gaze point positions of the subject detected when the diagnosis image 503 is being displayed is included in the left half region of the diagnosis image 503 (step S106). When 80% or more of the gaze point positions is not included in the left half region (No at step S106), the output controller 353 selects the diagnosis image 504, as the image to be displayed next, and displays the diagnosis image 504 (step S107). After displaying the diagnosis image 504, the output controller 353 displays the diagnosis image 505 (step S108). When 80% or more of the gaze point positions is included in the left half region (Yes at step S106), the output controller 353 skips the diagnosis image 504, selects the diagnosis image 505, as the image to be displayed next, and displays the diagnosis image 505 (step S108).

In the example of FIG. 8, the subject has looked at the right half by 80% or more. Therefore, the diagnosis image 504 is displayed next, and more accurate diagnosis is performed.

Next, the output controller 353 determines whether 80% or more of the gaze point positions of the subject detected when the diagnosis image 505 is being displayed is included in the region of the persons of the diagnosis image 505 (step S109). When 80% or more of the gaze point positions is not included in the region of the persons (No at step S109), the output controller 353 selects the diagnosis image 506, as the image to be displayed next, and displays the diagnosis image 506 (step S110). After displaying the diagnosis image 506, the output controller 353 displays the diagnosis image 507 (step S111). When 80% or more of the gaze point positions is included in the region of the persons (Yes at step S109), the output controller 353 skips the diagnosis image 506, selects the diagnosis image 507, as the image to be displayed next, and displays the diagnosis image 507 (step S111).

In the example of FIG. 8, the subject has looked at the pattern region by 80% or more. Therefore, the diagnosis image 506 is displayed next, and more accurate diagnosis is performed.

Next, the output controller 353 determines whether 80% or more of the gaze point positions of the subject detected when the diagnosis image 507 is being displayed id included in the region of the persons of the diagnosis image 507 (step S112). When 80% or more of the gaze point positions is not included in the region of the persons (No at step S112), the output controller 353 selects the diagnosis image 508, as the image to be displayed next, and displays the diagnosis image 508 (step S113). When 80% or more of the gaze point positions is included in the region of the persons (Yes at step S112), the output controller 353 skips display of the diagnosis image 508, and terminates the display of the diagnosis images.

In the example of FIG. 8, the subject has looked at the pattern region by 80% or more. Therefore, the diagnosis image 508 is displayed next, and more accurate diagnosis is performed.

The eye gaze detector 351 and the gaze point detector 352 terminate the detection operation of the eye gaze and the gaze point of the subject (step S114). The evaluator 354 calculates the evaluation values for the respective diagnosis images (step S115).

In the example of FIG. 8, the time to reproduce the diagnosis image 502 can be omitted. Therefore, the diagnosis time can be reduced from 80 seconds to 70 seconds.

Figure 9:
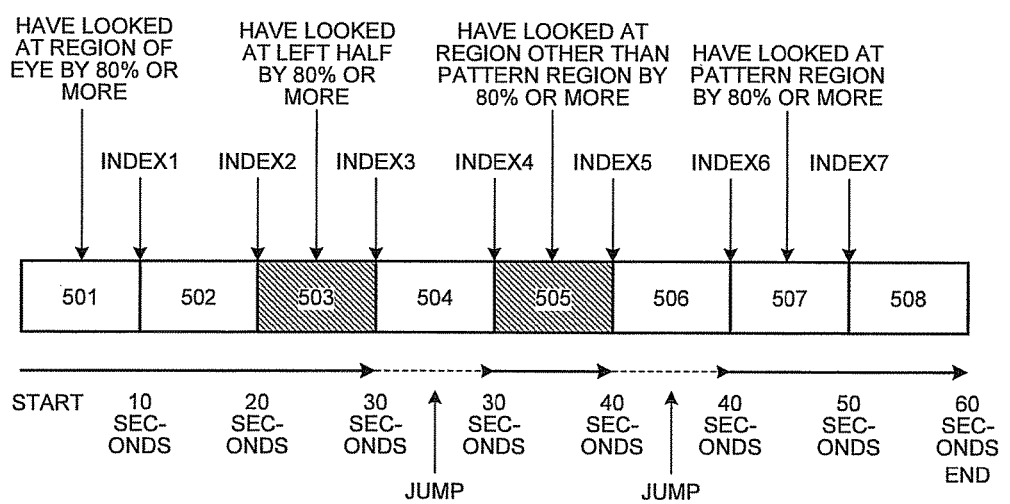
FIG. 9 is a diagram illustrating another example of a time chart of diagnosis images.

Next, another example of reduction of diagnosis time, using a time chart of FIG. 9, will be described. FIG. 9 is a diagram illustrating another example of a time chart of diagnosis images to be displayed.

The detection operation of the eye gaze and the gaze point of the subject is started (step S101). The output controller 353 displays the diagnosis image 501, and determines the gaze point positions of this time (step S103). In the example of FIG. 9, the subject has looked at the region other than the eye by 80% or more, the diagnosis image 502 is displayed next, and more accurate diagnosis is performed (step S104).

Next, the output controller 353 displays the diagnosis image 503 (step S105), and determines the gaze point positions of this time (step S106). In the example of FIG. 9, the subject has looked at the left half by 80% or more, and thus the subject has no tendency of the developmental disorder for the diagnosis image 503, or the diagnosis with the diagnosis image 503 is difficult. Therefore, the diagnosis with the next diagnosis image 504 is not effective. Therefore, the output controller 353 skips display of the diagnosis image 504, and jumps to the next picture position (INDEX 4). In the example of FIG. 9, the output controller 353 jumps from the INDEX 3 to the INDEX 4.

Next, the output controller 353 displays the diagnosis image 505 (step S108), and determines the gaze point positions of this time (step S109). In the example of FIG. 9, the subject has looked at the region other than the pattern region by 80% or more, and thus the subject has no tendency of the developmental disorder for the diagnosis image 505, or the diagnosis with the diagnosis image 505 is difficult. Therefore, the diagnosis with the next diagnosis image 506 is not effective. Therefore, the output controller 353 skips display of the diagnosis image 506, and jumps to the next picture position (INDEX 6). In FIG. 9, the output controller 353 jumps from the INDEX 5 to the INDEX 6.

Next, the output controller 353 displays the diagnosis image 507 (step S111), and determines the gaze point positions of this time (step S112). In the example of FIG. 9, the subject has looked at the pattern region by 80% or more, and thus the output controller 353 displays the diagnosis image 508, and more accurate diagnosis is performed (step S113).

Finally, the detection operation of the eye gaze and the gaze point of the subject is terminated (step S114), and the evaluator 354 calculates the evaluation values for the respective diagnosis images.

In the example of FIG. 9, the time to reproduce the diagnosis images 504 and 506 can be omitted, and thus the diagnosis time is reduced from 80 seconds to 60 seconds. As described above, the reduction of the diagnosis time can be achieved by skipping of unnecessary parts of the diagnosis images in accordance with each subject.

As described above, according to the first embodiment, effects as follows can obtained, for example.

(1) An item that enables more clear diagnosis support, in a plurality of determination algorithms having different arrangements of the person picture and the plurality of geometrical patterns, can be selectively presented, and the diagnosis time can be reduced.

(2) By the selective presentation of the item that enables clear diagnosis support, more accurate diagnosis support can be performed.

Second Embodiment

In a second embodiment, an eye gaze detection apparatus and an eye gaze detection method are realized, which can further simplify a device configuration compared with the first embodiment.

Hereinafter, an eye gaze detection apparatus and an eye gaze detection method according to the second embodiment will be described in detail based on the drawings. Note that the present invention is not limited by this embodiment. Hereinafter, an example of using an eye gaze detection apparatus, as a diagnosis supporting device that supports diagnosis of developmental disorder and the like, using eye gaze detection results, will be described. An applicable device is not limited to the diagnosis supporting device.

An eye gaze detection apparatus (diagnosis supporting device) according to the present embodiment detects an eye gaze, using an illuminator installed in one place. Further, the eye gaze detection apparatus (diagnosis supporting device) according to the present embodiment calculates a corneal curvature center position in a high accurate manner, using a result of measurement obtained by causing a subject to gaze at one point, before detection of the eye gaze.

Note that the illuminator is an element that includes a light source and can irradiate an eye ball of the subject with light. The light source is an element that emits light, such as a light emitting diode (LED). The light source may be configured from one LED, or may be configured such that a plurality of LEDs is combined and is arranged at one place. Hereinafter, "light source" may be used as a term that indicates the illuminator.

Figure 10:
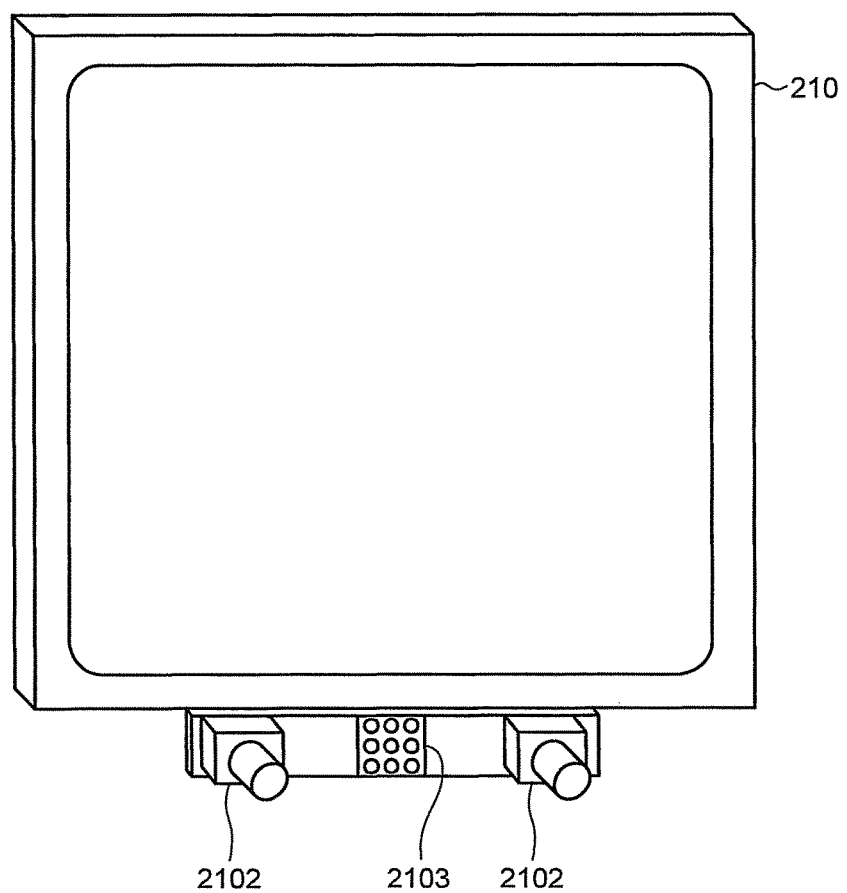
FIG. 10 is a diagram illustrating an example of an arrangement of a display, stereo cameras, an infrared light source of a second embodiment.
Figure 11:
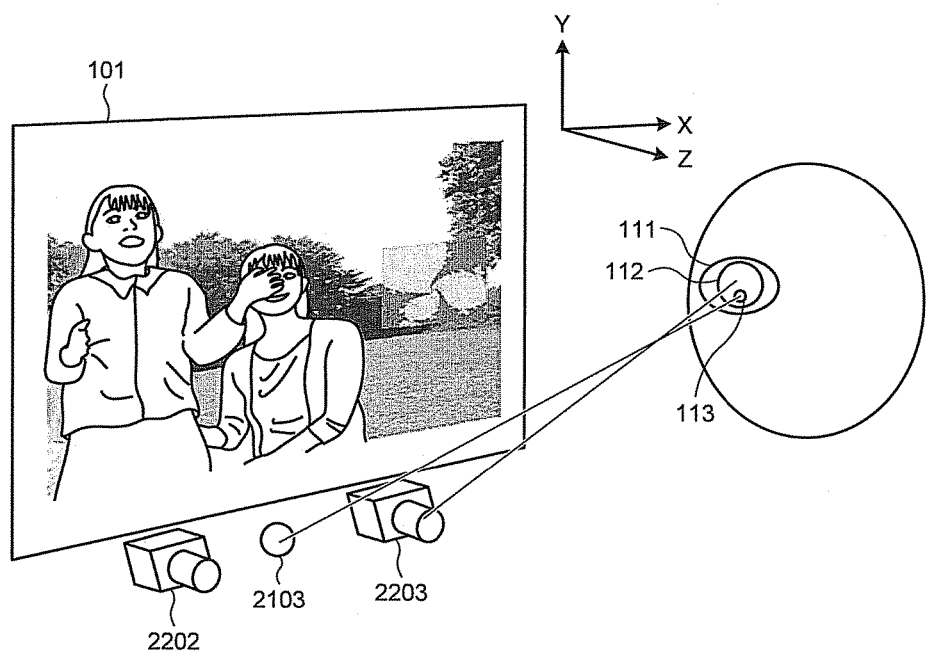
FIG. 11 is a diagram illustrating an example of an arrangement of the display, the stereo cameras, the infrared light source of the second embodiment, and a subject.

FIGS. 10 and 11 are diagrams illustrating an example of arrangement of a display, stereo cameras, an infrared light source of the second embodiment, and a subject. Note that the same configuration as the first embodiment is denoted with the same reference sign, and descriptions may be omitted.

As illustrated in FIG. 10, a diagnosis supporting device according to the second embodiment includes a display 210, a stereo camera 2102, and an LED light source 2103. The stereo camera 2102 is arranged under the display 210. The LED light source 2103 is arranged at a center position of two cameras included in the stereo camera 2102. The LED light source 2103 is, for example, a light source that irradiates the subject with a near infrared ray of wavelength 850 nm. FIG. 10 illustrates an example in which the LED light source 2103 (illuminator) is configured from nine LEDs. Note that, in the stereo camera 2102, a lens that can transmit near infrared light with a wavelength of 850 nm is used.

As illustrated in FIG. 11, the stereo camera 2102 includes a right camera 2202 and a left camera 2203. The LED light source 2103 irradiates an eye ball 111 of the subject with the near infrared light. In an image obtained by the stereo camera 2102, a pupil 112 is reflected at low luminance and becomes dark, and corneal reflection 113 caused in the eye ball 111, as a virtual image, is reflected at high luminance and becomes bright. Therefore, positions of the pupil 112 and the corneal reflection 113 on the image can be obtained by the two cameras (the right camera 2202 and the left camera 2203).

Further, three-dimensional world coordinate values of positions of a pupil 112 and a corneal reflection 113 are calculated from positions of the pupil 112 and the corneal reflection 113 obtained by the two cameras. In the present embodiment, as the three-dimensional world coordinates, a coordinate in an up and down direction is a Y coordinate (the up direction is +), a coordinate in a transverse direction is an X coordinate (the right direction is +), and a coordinate in a depth direction is a Z coordinate (the front side is +), where a middle position on a display screen 101 is an origin.

Figure 12:
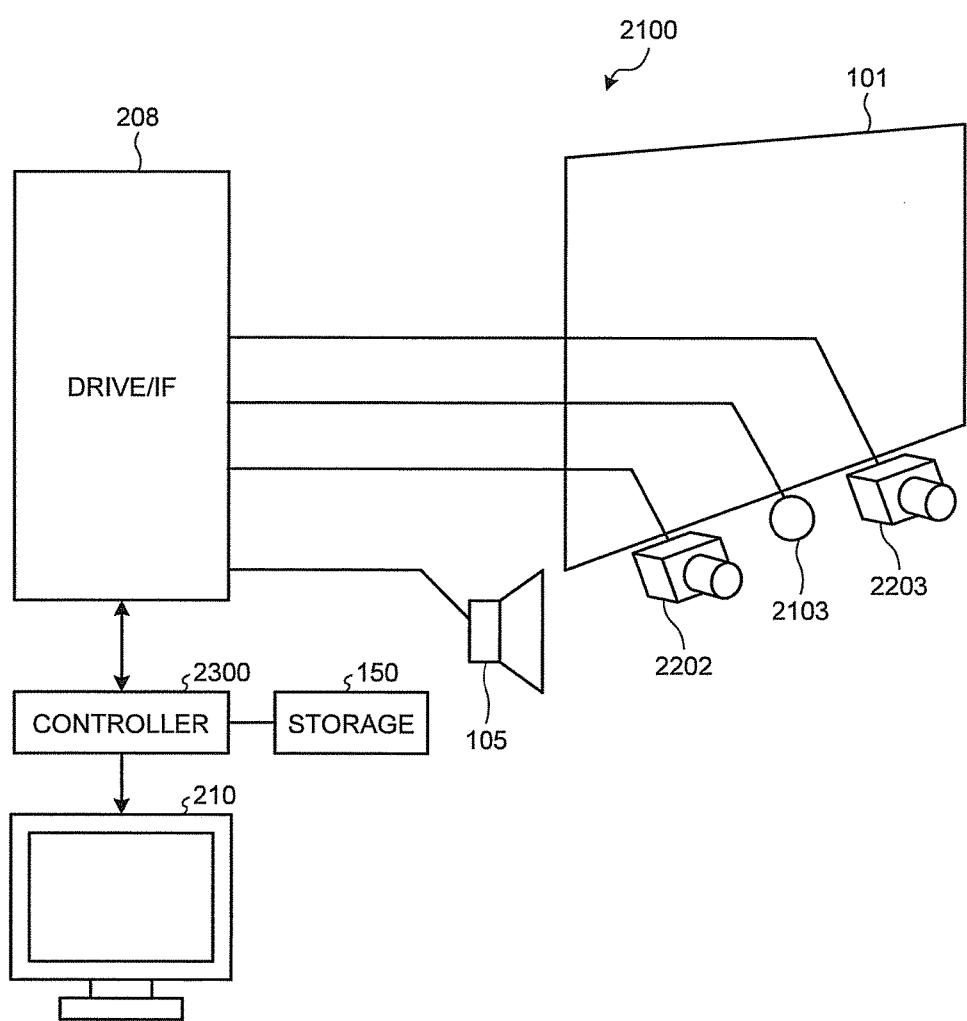
FIG. 12 is a diagram illustrating an outline of functions of a diagnosis supporting device.

FIG. 12 is a diagram illustrating an outline of functions of a diagnosis supporting device 2100 of the second embodiment. FIG. 12 illustrates a part of the configurations illustrated in FIGS. 10 and 11, and configurations used for driving the aforementioned configurations. As illustrated in FIG. 12, the diagnosis supporting device 2100 includes the right camera 2202, the left camera 2203, the LED light source 2103, a speaker 105, a drive/IF (interface) 208, a controller 2300, a storage 150, and the display 210. In FIG. 12, a positional relationship between a display screen 101, and the right camera 2202 and the left camera 2203 is illustrated in an easily understandable manner. The display screen 101 is a screen displayed in the display 210. Note that the driver and the IF may be integrated or separated.

The speaker 105 functions as an audio output unit that outputs an audio and the like for prompting the subject to pay attention, at the time of calibration and the like.

The drive/IF 208 drives units included in the stereo camera 2102. Further, the drive/IF 208 serves as an interface between the units included in the stereo camera 2102, and the controller 2300.

The controller 2300 can be realized by a computer that includes a control device such as a central processing unit (CPU), a storage device such as a read only memory (ROM) and a random access memory (RAM), a communication I/F that is connected with a network and performs communication, and a bus that connects the units.

The storage 150 stores various types of information such as a control program, a measurement result, and a diagnosis support result. The storage 150 stores an image to be displayed in the display 210, and the like. The display 210 displays various types of information such as an object image for diagnosis, and the like.

Figure 13:
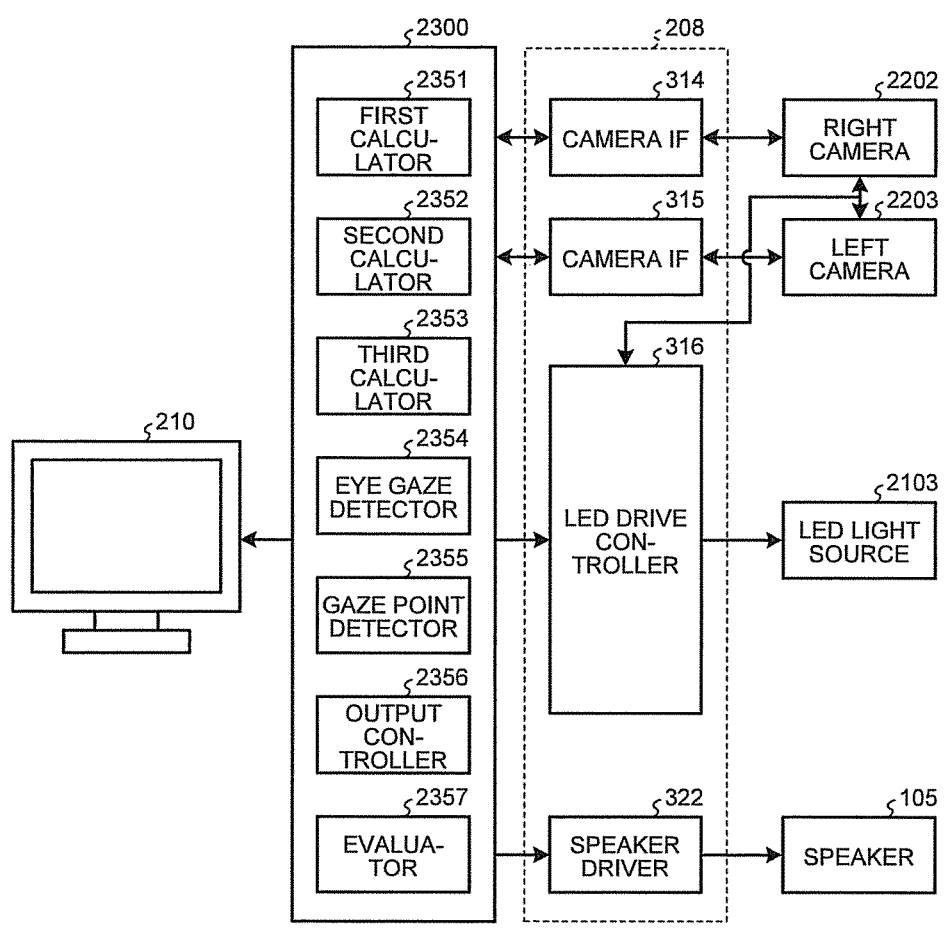
FIG. 13 is a block diagram illustrating an example of detailed functions of respective units illustrated in FIG. 12.

FIG. 13 is a block diagram illustrating an example of detailed functions of the respective units illustrated in FIG. 12. As illustrated in FIG. 13, the display 210 and the drive/IF 208 are connected to the controller 2300. The drive/IF 208 includes camera IFs 314 and 315, an LED drive controller 316, and a speaker driver 322.

The right camera 2202 and the left camera 2203 are connected to the drive/IF 208 through the camera IFs 314 and 315, respectively. The drive/IF 208 drives these cameras to capture the subject.

The speaker driver 322 drives the speaker 105. Note that the diagnosis supporting device 2100 may include an interface (printer IF) for being connected with a printer as a print unit. Further, the printer may be included inside the diagnosis supporting device 2100.

The controller 2300 controls the entire diagnosis supporting device 2100. The controller 2300 includes a first calculator 2351, a second calculator 2352, a third calculator 2353, an eye gaze detector 2354, a gaze point detector 2355, an output controller 2356, and an evaluator 2357. Note that at least the first calculator 2351, the second calculator 2352, the third calculator 2353, and the eye gaze detector 2354 may just be included as an eye gaze detection apparatus.

The elements (the first calculator 2351, the second calculator 2352, the third calculator 2353, the eye gaze detector 2354, the gaze point detector 2355, the output controller 2356, and the evaluator 2357) included in the controller 2300 may be realized by software (a program), may be realized by a hardware circuit, or may be realized by use of the software and the hardware circuit together.

When the elements are realized by the programs, the programs are recorded in a computer-readable recording medium such as a compact disk read only memory (CD-ROM), a flexible disk (FD), a compact disk recordable (CD-R), or a digital versatile disk (DVD) in a file in an installable format or in an executable format, and provided as a computer program product. The programs may be stored on a computer connected to a network such as the Internet, and provided by being downloaded through the network. Further, the programs may be provided or distributed through the network such as the Internet. Further, the programs may be configured to be provided by being incorporated in ROM or the like in advance.

The first calculator 2351 calculates a position (first position) of a pupil center that indicates a center of a pupil, from an image of an eye ball captured by a stereo cameras 2102. The second calculator 2352 calculates a position (second position) of a corneal reflection center that indicates a center of a corneal reflection, from the captured image of an eye ball. The first calculator 2351 and the second calculator 2352 correspond to a position detector that detects the first position that indicates the center of the pupil and the second position that indicates the center of the corneal reflection.

The third calculator 2353 calculates a corneal curvature center (fourth position), from a straight line (first straight line) that connects an LED light source 2103 and the corneal reflection center. For example, the third calculator 2353 calculates a position where a distance from the corneal reflection center becomes a predetermined value, on the straight line, as the corneal curvature center. As the predetermined value, a value determined in advance from a curvature radius value of a typical cornea can be used.

An individual difference may be caused in the curvature radius value of a cornea. Therefore, there is a possibility that an error becomes large when the corneal curvature center is calculated using the value determined in advance. Therefore, the third calculator 2353 may calculate the corneal curvature center in consideration of the individual difference. In this case, the third calculator 2353 first calculates an intersection point of a straight line (second straight line) that connects the pupil center and a target position, and straight line that connects the corneal reflection center and the LED light source 2103, using the pupil center and the corneal reflection center calculated when the subject is caused to gaze at a target position (third position). The third calculator 2353 then calculates a distance (first distance) between the pupil center and the calculated intersection point, and stores the calculated distance in a storage 150, for example.

The target position may be any position as long as the position can be determined in advance, and three-dimensional world coordinate values can be calculated. For example, a middle position (the origin of the three-dimensional world coordinates) of the display screen 101 can be used as the target position. In this case, for example, the output controller 2356 displays an image (target image) or the like that the subject is caused to gaze at, in the target position (center) on the display screen 101. Accordingly, the subject can be caused to gaze at the target position.

The target image may be any image as long as the image can draw attention from the subject. For example, an image with a varying display form such as luminance or a color, an image having different display form from other regions, or the like can be used as the target image.

Note that the target position is not limited to the center of the display screen 101, and any position can be employed. If the center of the display screen 101 is employed as the target position, the distance between the center and any end part of the display screen 101 is minimized. Therefore, for example, a measurement error at the time of detecting the eye gaze can be made smaller.

The processing up to the calculation of the distance is executed in advance before actual detection of an eye gaze is started, for example. At the time of actual detection of an eye gaze, the third calculator 2353 calculates a position where the distance from the pupil center becomes the distance calculated in advance, on the straight line that connects the LED light source 2103 and the corneal reflection center, as the corneal curvature center. The third calculator 2353 corresponds to a calculator that calculates the corneal curvature center (fourth position), from the position of the LED light source 2103, the predetermined position (third position) that indicates the target image on the display, the position of the pupil center, and the position of the corneal reflection center.

The eye gaze detector 2354 detects the eye gaze of the subject from the pupil center and the corneal curvature center. For example, the eye gaze detector 2354 detects a direction from the corneal curvature center toward the pupil center, as an eye gaze direction of the subject.

The gaze point detector 2355 detects a gaze point of the subject, using the detected eye gaze direction. The gaze point detector 2355 detects, for example, a gaze point that is a point that the subject gazes at on the display screen 101. The gaze point detector 2355 detects an intersection point of an eye gaze vector and an XY plane, which are expressed in a three-dimensional world coordinate system as illustrated in FIG. 11, as the gaze point of the subject.

The output controller 2356 controls output of various types of information to the display 210, the speaker 105, and the like. For example, the output controller 2356 outputs the target image to the target position on the display 210. Further, the output controller 2356 controls output to the display 210, such as a diagnosis image, an evaluation result by the evaluator 2357, and the like.

The diagnosis image may just be an image according to evaluation processing based on an eye gaze (gaze point) detection result. For example, when a developmental disorder is diagnosed, a diagnosis image that includes an image (a geometrical pattern picture or the like) preferred by the subject with the developmental disorder, and another image (a picture of a person, or the like) may be used.

The evaluator 2357 performs evaluation processing based on the diagnosis image, and the gaze point detected by the gaze point detector 2355. For example, when the developmental disorder is diagnosed, the evaluator 2357 analyzes the diagnosis image and the gaze point, and evaluates whether the subject with the developmental disorder has gazed at the image that the subject prefers.

The output controller 2356 may display a diagnosis image similar to the first embodiment, and the evaluator 2357 may perform evaluation processing similar to the evaluator 354 of the first embodiment. In other words, the eye gaze detection processing (eye gaze detector 351) of the first embodiment may be replaced with the eye gaze detection processing (the first calculator 2351, the second calculator 2352, the third calculator 2353, and the eye gaze detector 2354) of the second embodiment. Accordingly, an effect of the second embodiment (simplification of the device configuration, and the like) can be achieved in addition to the effect of the first embodiment.

Figure 14:
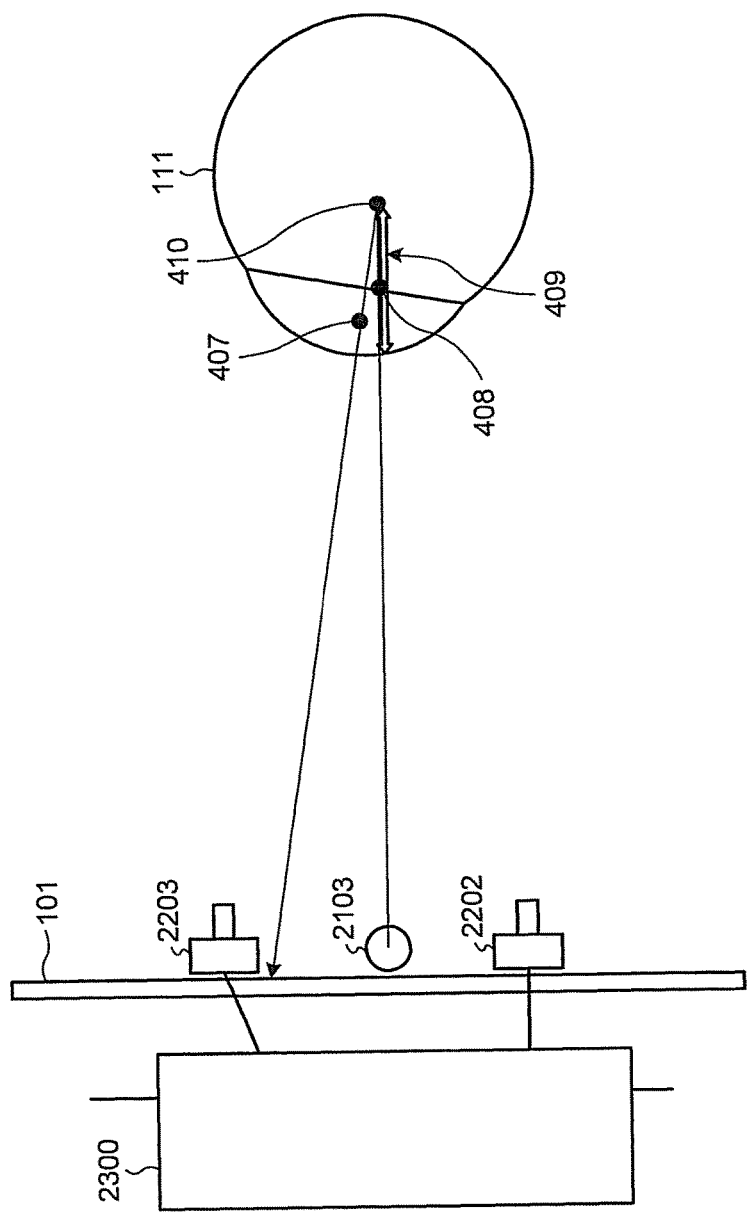
FIG. 14 is a diagram illustrating an outline of processing executed by the diagnosis supporting device of the second embodiment.

FIG. 14 is a diagram for describing an outline of processing executed by the diagnosis supporting device 2100 of the present embodiment. Elements described in FIGS. 10 to 13 are denoted with the same reference signs, and descriptions are omitted.

A pupil center 407 and a corneal reflection center 408 respectively indicate the center of the pupil and the center of a corneal reflection point detected when the LED light source 2103 is lighted. A cornea curvature radius 409 indicates the distance from a surface of the cornea to a corneal curvature center 410.

Figure 15:
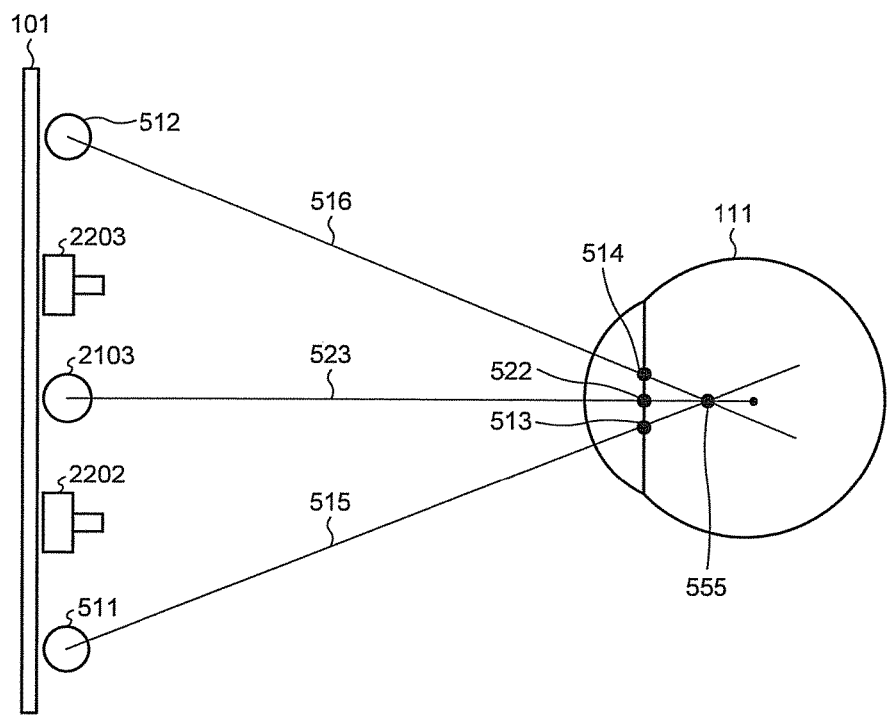
FIG. 15 is an explanatory diagram illustrating a difference between a method of using two light sources and the second embodiment using one light source.

FIG. 15 is an explanatory diagram illustrating a difference between a method using two light sources (illuminators) (hereinafter, referred to as method A), and the present embodiment using one light source (illuminator). Elements described in FIGS. 10 to 13 are denoted with the same reference signs, and descriptions are omitted.

The method A uses two LED light sources 511 and 512, in place of the LED light source 2103. In the method A, an intersection point of a straight line 515 that connects a corneal reflection center 513 and the LED light source 511 of when the LED light source 511 irradiates the subject with light, and a straight line 516 that connects a corneal reflection center 514 and the LED light source 512 of when the LED light source 512 irradiates the subject with light is calculated. This intersection point serves as a corneal curvature center 555.

In contrast, in the present embodiment, a straight line 523 that connects a corneal reflection center 522 and the LED light source 2103 of when the LED light source 2103 irradiates the subject with light is considered. The straight line 523 passes through the corneal curvature center 555. Further, the curvature radius of a cornea is known to have a small influence due to the individual difference and have a nearly fixed value. According to this fact, the corneal curvature center of when the LED light source 2103 irradiates the subject with light exists on the straight line 523, and can be calculated using a typical curvature radius value.

However, when the gaze point is calculated using the position of the corneal curvature center obtained using the typical curvature radius value, the gaze point position is deviated from an original position due to the individual difference of the eye ball, and an accurate gaze point position may not be able to be detected.

Figure 16:
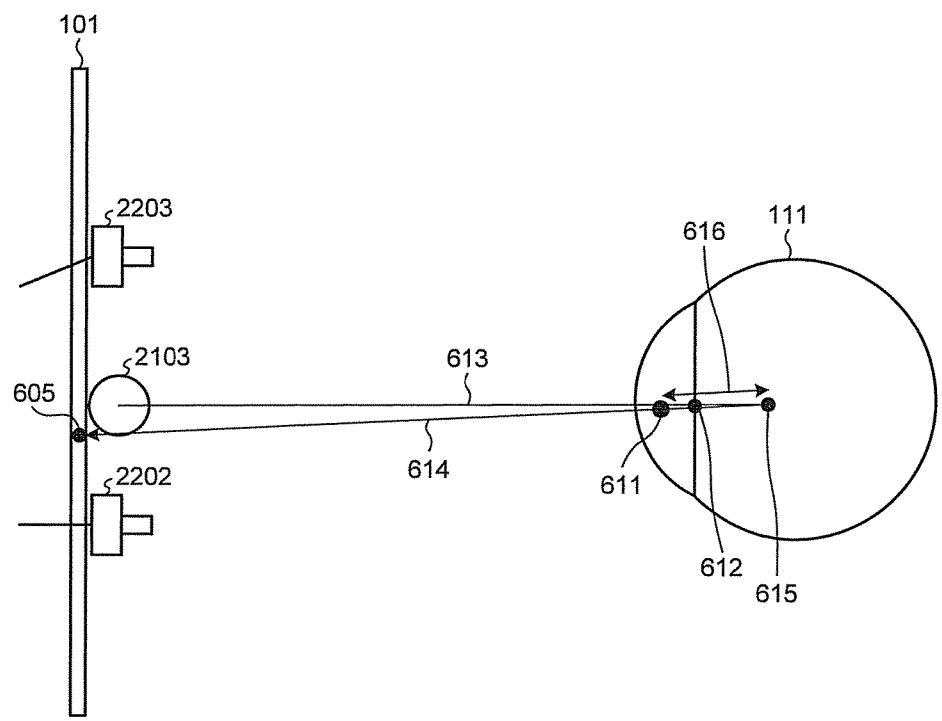
FIG. 16 is a diagram for describing calculation processing of calculating a distance between a pupil center position and a corneal curvature center position.

FIG. 16 is a diagram for describing calculation processing of calculating a corneal curvature center position, and the distance between a pupil center position and the corneal curvature center position, before the gaze point detection (eye gaze detection) is performed. Elements described in FIGS. 10 to 13 are denoted with the same reference signs, and descriptions are omitted. Note that connection of the right and left cameras (the right camera 2202 and the left camera 2203) and the controller 2300 is not illustrated and is omitted.

A target position 605 is a position for causing the subject to gaze at, by an output of a target image or the like to one point on the display 210. In the present embodiment, the target position 605 is a middle position on the display screen 101. A straight line 613 is a straight line that connects the LED light source 2103 and a corneal reflection center 612. A straight line 614 is a straight line that connects the target position 605 (gaze point) that the subject gazes at and a pupil center 611. A corneal curvature center 615 is an intersection point of the straight line 613 and the straight line 614. The third calculator 2353 calculates and stores a distance 616 between the pupil center 611 and the corneal curvature center 615.

Figure 17:
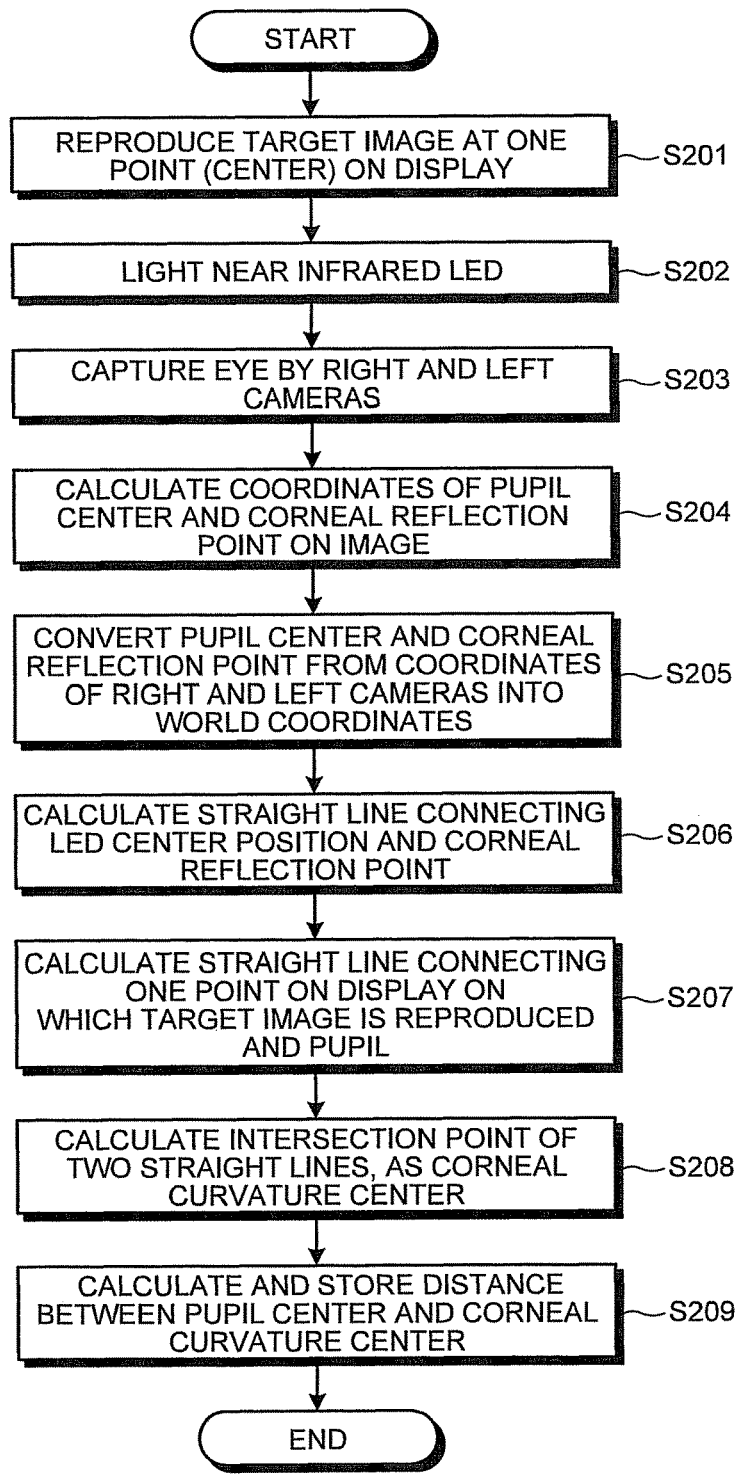
FIG. 17 is a flowchart illustrating an example of the calculation processing of the second embodiment.

FIG. 17 is a flowchart illustrating an example of calculation processing of the present embodiment.

First, the output controller 2356 reproduces the target image at one point on the display screen 101 (step S201), and prompts the subject to gaze at the one point. Next, the controller 2300 lights the LED light source 2103 toward an eye of the subject, using an LED drive controller 316 (step S202). The controller 2300 captures the eye of the subject by the right and left cameras (the right camera 2202 and the left camera 2203) (step S203).

By the irradiation of the LED light source 2103, a pupil part is detected as a dark part (dark pupil). Further, a virtual image of corneal reflection is caused as reflection of the LED irradiation, and a corneal reflection point (corneal reflection center) is detected as a bright part. That is, the first calculator 2351 detects the pupil part from the captured image, and calculates coordinates that indicate the position of the pupil center. The first calculator 2351 detects a region having predetermined brightness or less including a darkest part in a fixed region including the eye, as the pupil part, and a region having predetermined brightness or more including a brightest part, as the corneal reflection. Further, the second calculator 2352 detects a corneal reflection part from the captured image, and calculates coordinates that indicate the position of the corneal reflection center. Note that the first calculator 2351 and the second calculator 2352 calculate respective coordinate values for two images obtained by the right and left cameras (step S204).

Note that the right and left cameras are subjected to camera calibration by a stereo calibration method in order to acquire the three-dimensional world coordinates, and a conversion parameter is calculated. As the stereo calibration method, any conventionally used method can be applied, such as a method using the Tsai's calibration theory or the like.

The first calculator 2351 and the second calculator 2352 convert the coordinates of the right and left cameras into three-dimensional world coordinates of the pupil center and the corneal reflection center, using the conversion parameter (step S205). The third calculator 2353 obtains a straight line that connects the obtained world coordinates of the corneal reflection center, and world coordinates of a center position of the LED light source 2103 (step S206). Next, the third calculator 2353 calculates a straight line that connects world coordinates of a center of the target image displayed at the one point on the display screen 101, and the world coordinates of the pupil center (step S207). The third calculator 2353 obtains an intersection point of the straight line calculated at step S206 and the straight line calculated at step S207, and employs this intersection point as the corneal curvature center (step S208). The third calculator 2353 calculates a distance between the pupil center and the corneal curvature center of this time, and stores the calculated distance in the storage 150, or the like (step S209). The stored distance is used to calculate the corneal curvature center at a subsequent time of detection of a gaze point (eye gaze).

The distance between the pupil center and the corneal curvature center of when the subject gazes at the one point on the display 210 in the calculation processing is constantly maintained within a range of detecting the gaze point in the display 210. The distance between the pupil center and the corneal curvature center may be obtained from an average of entire values calculated during the reproduction of the target image, or may be obtained from an average of values of several times, of values calculated during the reproduction.

Figure 18:
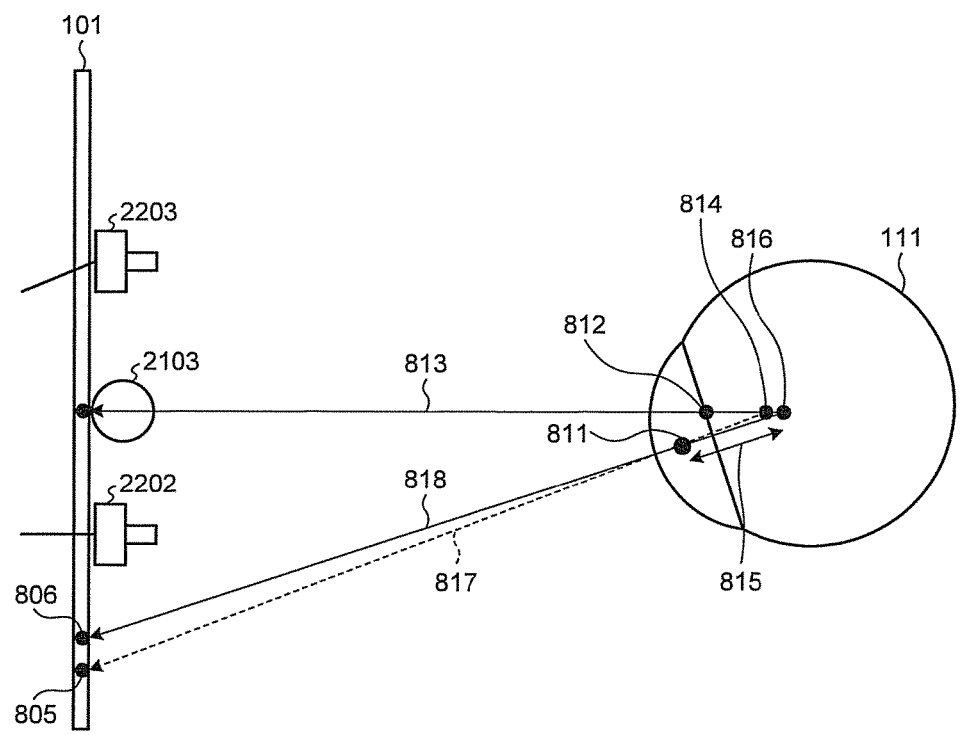
FIG. 18 is a diagram illustrating a method of calculating a corneal curvature center position using a distance obtained in advance.

FIG. 18 is a diagram illustrating a method of calculating a position of a corrected corneal curvature center, using the distance between the pupil center and the corneal curvature center obtained in advance, when the gaze point is detected. A gaze point 805 indicates the gaze point obtained from the corneal curvature center calculated using the typical curvature radius value. A gaze point 806 indicates the gaze point obtained from the corneal curvature center calculated using the distance obtained in advance.

A pupil center 811 and a corneal reflection center 812 respectively indicate the position of the pupil center and the position of the corneal reflection center calculated at the time of detecting the gaze point. A straight line 813 is a straight line that connects the LED light source 2103 and the corneal reflection center 812. A corneal curvature center 814 is the position of the corneal curvature center calculated from the typical curvature radius value. A distance 815 is the distance between the pupil center and the corneal curvature center calculated in the previous calculation processing. A corneal curvature center 816 is the position of the corneal curvature center calculated using the distance obtained in advance. The corneal curvature center 816 is obtained from the facts that the corneal curvature center exists on the straight line 813, and the distance between the pupil center and the corneal curvature center is the distance 815. Accordingly, an eye gaze 817 calculated when the typical curvature radius value is used is corrected to an eye gaze 818. Further, the gaze point on the display screen 101 is corrected from the gaze point 805 to the gaze point 806. Note that connection of the right and left cameras (the right camera 2202 and the left camera 2203) and the controller 2300 is not illustrated and omitted.

Figure 19:
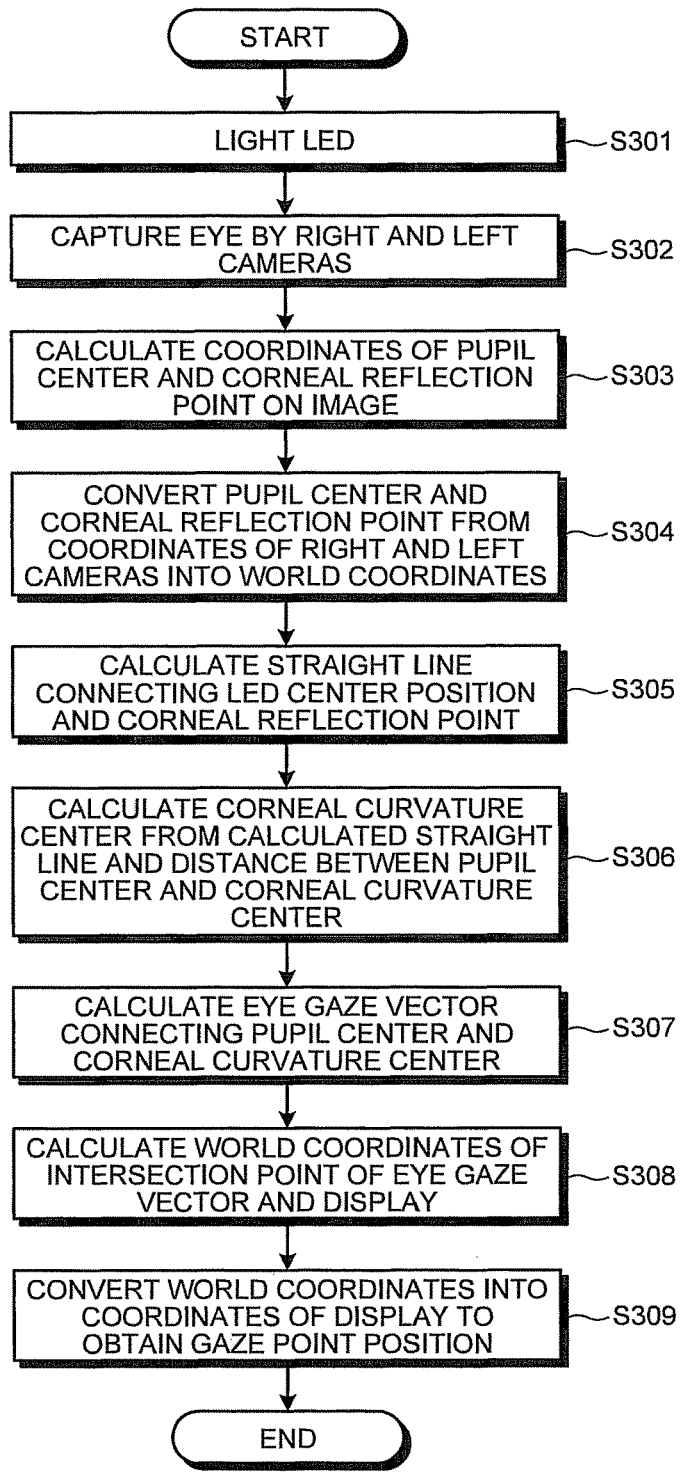
FIG. 19 is a flowchart illustrating an example of eye gaze detection processing of the second embodiment.

FIG. 19 is a flowchart illustrating an example of eye gaze detection processing of the present embodiment. For example, as processing of detecting an eye gaze in diagnosis processing using a diagnosis image, the eye gaze detection processing of FIG. 19 can be executed. In the diagnosis processing, processing of displaying a diagnosis image, evaluation processing by the evaluator 2357 using the detection result of the gaze point, and the like are executed, in addition to the steps of FIG. 19.

Steps S301 to S305 are similar to steps S202 to S206 of FIG. 17, and thus descriptions are omitted.

The third calculator 2353 calculates a position on the straight line calculated at step S305, and in which the distance from the pupil center is equal to the distance obtained in the previous calculation processing, as the corneal curvature center (step S306).

The eye gaze detector 2354 obtains a vector (eye gaze vector) that connects the pupil center and the corneal curvature center (step S307). This vector indicates the eye gaze direction that the subject is looking at. The gaze point detector 2355 calculates three-dimensional world coordinate values of an intersection point of the eye gaze direction and the display screen 101 (step S308). The values are coordinate values that express the one point on the display 210 that the subject gazes at, in the world coordinates. The gaze point detector 2355 converts the obtained three-dimensional world coordinate values into coordinate values (x, y) expressed in a two-dimensional coordinate system of the display 210 (step S309). Accordingly, the gaze point on the display 210 that the subject gazes at can be calculated.

Calculation processing of calculating the distance between the pupil center position and the corneal curvature center position is not limited to the method described in FIGS. 16 and 17. Hereinafter, another example of calculation processing will be described using FIGS. 20 and 21.

Figure 20:
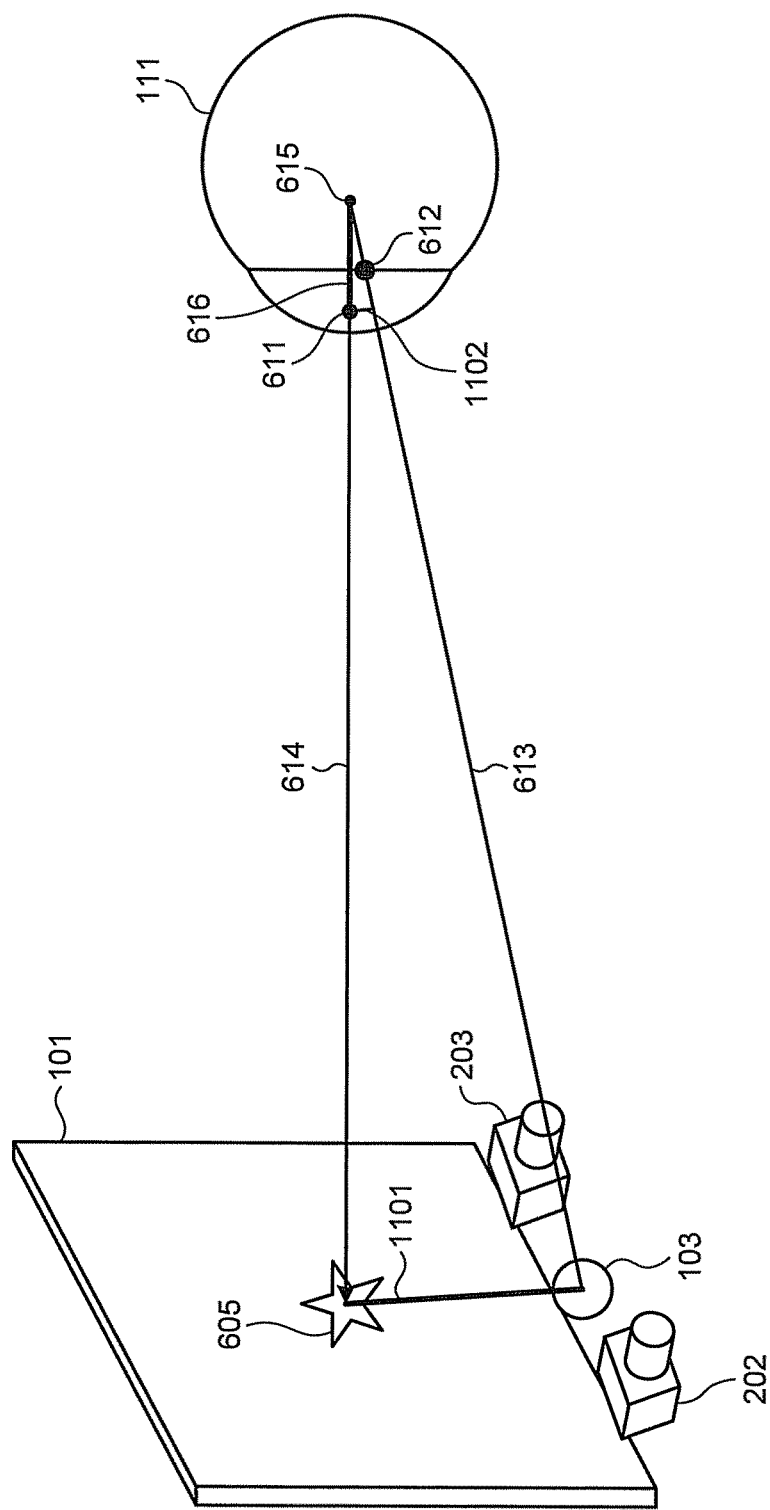
FIG. 20 is a diagram for describing calculation processing of a modification.

FIG. 20 is a diagram for describing calculation processing of the present modification. Elements described in FIGS. 10 to 13, and 16 are denoted with the same reference signs, and descriptions are omitted.

A line segment 1101 is a line segment (first line segment) that connects a target position 605 and an LED light source 103. A line segment 1102 is a line segment (second line segment) that is parallel to the line segment 1101, and connects a pupil center 611 and a straight line 613. In the present modification, a distance 616 between the pupil center 611 and a corneal curvature center 615 is calculated using the line segment 1101 and the line segment 1102, and stored.

Figure 21:
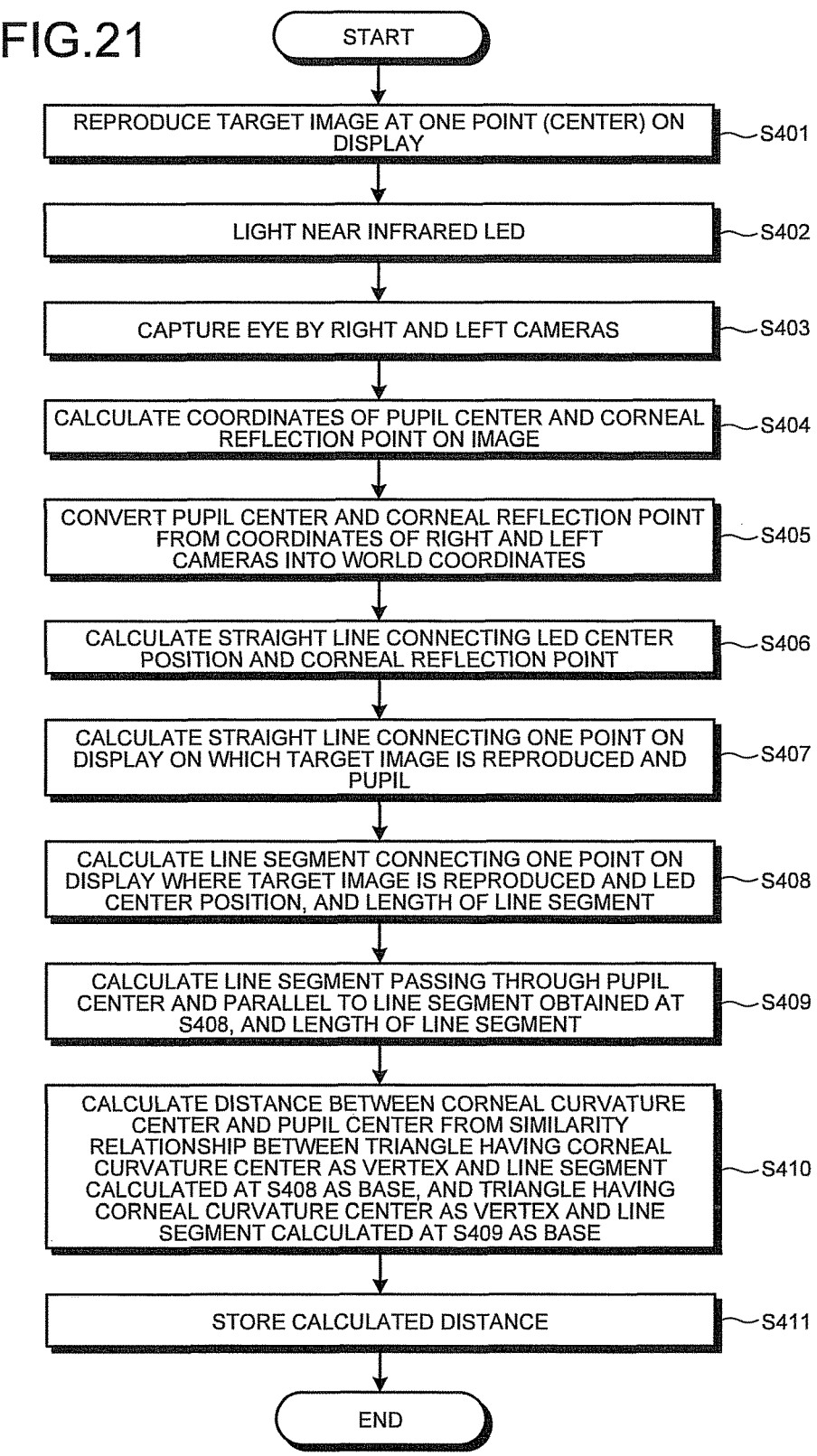
FIG. 21 is a flowchart illustrating an example of the calculation processing of the modification.

FIG. 21 is a flowchart illustrating an example of calculation processing of the present modification.

Steps S401 to S407 are similar to steps S201 to S207 of FIG. 17, and thus descriptions are omitted.

A third calculator 2353 calculates a line segment (the line segment 1101 in FIG. 20) that connects a center of a target image displayed in one point on a screen of a display 210, and a center of the LED light source 103, and calculates a length (L1101) of the calculated line segment (step S408).

The third calculator 2353 calculates a line segment (the line segment 1102 in FIG. 20) that passes through the pupil center 611, and is parallel to the line segment calculated at step S408, and calculates a length (L1102) of the calculated line segment (step S409).

The third calculator 2353 calculates the distance 616 between the pupil center 611 and the corneal curvature center 615, based on the fact that a triangle having the corneal curvature center 615 as a vertex, and the line segment calculated at step S408 as a base, and a triangle having the corneal curvature center 615 as a vertex, and the line segment calculated at step S409 as a base have a similarity relationship (step S410). For example, the third calculator 2353 calculates the distance 616 such that a ratio of the length of the line segment 1102 to the length of the line segment 1101, and a ratio of the distance 616 to a distance between the target position 605 and the corneal curvature center 615 become equal.

The distance 616 can be calculated by the following formula (1). Note that L614 is the distance from the target position 605 to the pupil center 611.

$$\text{The distance } 616 = (L614 \times L1102)/(L1101 \times L1102) \quad (1)$$

The third calculator 2353 stores the calculated distance 616 in a storage 150 and the like (step S411). The stored distance is used to calculate the corneal curvature center at a subsequent time of detection of a gaze point (eye gaze).

As described above, according to the present embodiment, effects as follows can obtained, for example.
(1) It is not necessary to arrange the light source (illuminator) in two places, and detection of an eye gaze can be performed with the light source arranged in one place.
(2) Because the light source is arranged in one place, the device can be made compact, and a decrease in cost can be realized.

Although the invention has been described with respect to specific embodiments for a complete and clear disclosure, the appended claims are not to be thus limited but are to be construed as embodying all modifications and alternative constructions that may occur to one skilled in the art that fairly fall within the basic teaching herein set forth.

What is claimed is:
1. A diagnosis supporting device comprising:
a display;
a stereo camera configured to capture an image of a subject;
an eye gaze detector configured to detect an eye gaze direction of the subject, from the image captured by the stereo camera;
a gaze point detector configured to detect a gaze point of the subject in a display region of the display based on the eye gaze direction;
an output controller configured to
display any of a plurality of diagnosis images on the display,
select a diagnosis image, of the plurality of diagnosis images, to be displayed next according to a position of the gaze point detected when the diagnosis image is displayed, and
display the diagnosis image on the display; and
an evaluator configured to calculate, for the respective diagnosis images, an evaluation value of the subject that corresponds to a degree of a development disorder and a ratio of looking at a predetermined region within the diagnosis image based on the gaze point detected by the gaze point detector when the diagnosis image is displayed,
wherein
each of the plurality of diagnosis images belongs to one out of a plurality of groups, and
the output controller selects,
when the diagnosis image belonging to a first group, of the plurality of groups, which includes similar diagnosis images used to calculate a similar evaluation value is displayed, and, further,
when a ratio of positions of the gaze point indicates that a number of the gaze points detected in a predetermined region in the diagnosis image and in a predetermined period is equal to or greater than a predetermined threshold,
another diagnosis image belonging to the first group as the diagnosis image to be displayed next, and
when the ratio of the positions of the gaze point indicates that the number of the gaze point detected in the predetermined region in the diagnosis image and in the predetermined period is less than the predetermined threshold,
a diagnosis image belonging to a second group, of the plurality of groups, that is different than the first group as the diagnosis image to be displayed next,
wherein the ratio is a ratio of the number of gaze points detected in the predetermined region to a total number of the detected gaze points, or a ratio of a total time in which the gaze point is detected within the predetermined region to a total time in which the gaze point is detected.

2. The diagnosis supporting device according to claim 1, wherein
the diagnosis image includes an image of a person and an image of a geometrical pattern,
the first group includes a first diagnosis image and a second diagnosis image in which a position of the image of the person and a position of the image of the geometrical pattern are symmetrical about a line that passes through a vicinity of a center of the diagnosis image in an up and down direction, and
the output controller selects, according to the position of the gaze point detected when the first diagnosis image classified into the first group is displayed, one of the second diagnosis image or the diagnosis image classified in the second group as the diagnosis image to be displayed next.

3. The diagnosis supporting device according to claim 1, further comprising:
   an illuminator including a light source that performs irradiation of light;
   a target position provided on the display;
   a position detector configured to calculate a first position indicating a center of a pupil and a second position indicating a center of a corneal reflection, from an image of an eye ball of the subject irradiated with the light by the illuminator and captured by the stereo camera; and
   a calculator configured to calculate a third position indicating a curvature center of a cornea as an intersection point of a straight line that connects the first position and the target position, and a straight line that connects the second position and a position of the light source, wherein
   the eye gaze detector detects an eye gaze of the subject based on the first position and the third position.

4. The diagnosis supporting device according to claim 1, wherein
   the output controller is configured to, when the ratio of the positions of the gaze point not included in the predetermined region is equal to or greater than than the predetermined threshold in a last diagnosis image included in the first group, select a diagnosis image from the second group to be displayed next.

5. A method of supporting diagnosis, the method comprising:
   an eye gaze detection step of detecting an eye gaze direction of a subject from a captured image captured by a stereo camera that captures the subject;
   a gaze point detection step of detecting a gaze point of the subject in a display region of a display based on the eye gaze direction;
   an output control step of displaying any of a plurality of diagnosis images on the display, selecting a diagnosis image, of the plurality of diagnosis images, to be displayed next according to a position of the gaze point detected when the diagnosis image is displayed, and displaying the selected diagnosis image on the display; and
   an evaluation step of calculating, for the respective diagnosis images, an evaluation value of the subject that corresponds to a degree of a developmental disorder and a ratio of looking at a predetermined region within the diagnosis image based on the gaze point detected in the gaze point detection step when the diagnosis image is displayed, wherein
   each of the plurality of diagnosis images belongs to one of a plurality of groups, and
   the output control step selects,
      when the diagnosis image belonging to a first group which includes similar diagnosis images used to calculate a similar evaluation value is displayed, and, further,
      when a ratio of positions of the gaze point indicates that a number of the gaze points detected in a predetermined region in the diagnosis image and in a predetermined period is equal to or greater than a predetermined threshold,
         another diagnosis image belonging to the first group as the diagnosis image to be displayed next, and
      when the ratio of positions of the gaze point indicates that the number of the gaze point detected in the predetermined region in the diagnosis image and in the predetermined period is less than the predetermined threshold,
         a diagnosis image belonging to a second group, of the plurality of groups, different from the first group as the diagnosis image to be displayed next, wherein
   the ratio is a ratio of the number of gaze points detected in the predetermined region to a total number of the detected gaze points, or a ratio of a total time in which the gaze point is detected within the predetermined region to a total time in which the gaze point is detected.

6. The method of supporting diagnosis according to claim 5, wherein
   the output control step selects a diagnosis image to be displayed next included in the second group if the ratio of the positions of the gaze point not included in the predetermined region is equal to or greater than than the predetermined threshold in a last diagnosis image included in the first group.

* * * * *